US008741305B2

(12) United States Patent
Thomas et al.

(10) Patent No.: US 8,741,305 B2
(45) Date of Patent: Jun. 3, 2014

(54) PROTEIN COMPOSITION FOR INDUCING AN IMMUNE RESPONSE IN A VERTEBRATE COMPRISING A PLURALITY OF PROTEIN VARIANTS COVERING THE HETEROGENEITY OF A SINGLE ANTIGEN, AMA1

(75) Inventors: Alan William Thomas, Bishop (NL); Clemens Hendricus Martinus Kocken, Moerkapelle (NL); Bart Willem Faber, Den Haag (NL); Edmond Joseph Remarque, Leiden (NL)

(73) Assignee: Stichting Biomedical Primate Research Centre, Rijswijk (NL)

( * ) Notice: Subject to any disclaimer, the term of this patent is extended or adjusted under 35 U.S.C. 154(b) by 1040 days.

(21) Appl. No.: 12/520,344

(22) PCT Filed: Dec. 21, 2006

(86) PCT No.: PCT/EP2006/012444
§ 371 (c)(1),
(2), (4) Date: Mar. 4, 2010

(87) PCT Pub. No.: WO2008/074356
PCT Pub. Date: Jun. 26, 2008

(65) Prior Publication Data
US 2010/0172923 A1 Jul. 8, 2010

(51) Int. Cl.
*A61K 39/00* (2006.01)
*A61K 39/002* (2006.01)
(52) U.S. Cl.
USPC ...................................................... 424/191.1
(58) Field of Classification Search
None
See application file for complete search history.

(56) References Cited

FOREIGN PATENT DOCUMENTS

| EP | 1669370 A1 | 6/2006 |
|---|---|---|
| WO | 9521192 A1 | 8/1995 |
| WO | 02052014 A2 | 7/2002 |

OTHER PUBLICATIONS

Lalitha et al. ( Infection and Immunity, vol. 72, No. 8, pp. 4464-4470, Aug. 2004.*
Kennedy et al., "In Vitro Studies with Recombinant Plasmodium falciparum Apical Membrane Antigen 1 (AMA1): Production and Activity of an AMA1 Vaccine and Generation of a Multiallelic Response", Infection and Immunity, (Dec. 2002), vol. 70, No. 12, pp. 6948-6960.
Hodder et al., "Specificity of the Protective Antibody Response to Apical Membrane Antigen 1", Infection and Immunity, (May 2001), vol. 69, No. 5, pp. 3286-3294.
Eisen et al., "A Plasmodium falciparum apical membrane antigen-1 (AMA-1) gene apparently generated by intragenic recombination", Molecular and Biochemical Parasitology, (Feb. 1999), vol. 100, pp. 243-246.
Cortes et al., "Geographical Structure of Diversity and Differences between Symptomatic and Asymptomatic Infections for *Plasmodium falciparum* Vaccine Candidate AMA1", Infection and Immunity, (Mar. 2003), vol. 71, No. 3., pp. 1416-1426.
Healer et al., "Allelic polymorphisms in apical membrane antigen-1 are responsible for evasion of antibody-mediated inhibition in *Plasmodium falciparum*", Molecular Microbiology, (2004), vol. 52, No. 1, pp. 159-168.
Kocken et al., "High-Level Expression of the Malaria Blood-Stage Vaccine Candidate *Plasmodium falciparum* Apical Membrane Antigen 1 and Induction of Antibodies That Inhibit Erythrocyte Invasion", Infection and Immunity, (Aug. 2002), vol. 70, No. 8, pp. 4471-4476.
Marshall et al., "Diversity of the vaccine candidate AMA-1 of *Plasmodium falciparum*", Molecular and Biochemical Parasitology, (Jan. 1996), vol. 77, pp. 109-113.
Escalante et al., "Polymorphism in the gene encoding the apical membrane antigen-1 (AMA-1) of *Plasmodium falciparum*. X. Asembo Bay Cohort Project", Molecular & Biochemical Parasitology, (Jan. 2001), vol. 113, pp. 279-287.
Malkin et al., "Phase 1 Clinical Trial of Apical Membrane Antigen 1: an Asexual Blood-Stage Vaccine for *Plasmodium falciparum* Malaria", Infection and Immunity, (Jun. 2005), vol. 73, No. 6, pp. 3677-3685.
Dutta et al., "Purification, Characterization, and Immunogenicity of the Refolded Ectodomain of the *Plasmodium falciparum* Apical Membrane Antigen 1 Expressed in *Escherichia coli*", Infection and Immunity, (Jun. 2002), vol. 70, No. 6, pp. 3101-3110.

* cited by examiner

*Primary Examiner* — Gary B. Nickol
*Assistant Examiner* — Khatol Shahnan-Shah
(74) *Attorney, Agent, or Firm* — The Webb Law Firm

(57) ABSTRACT

The present invention relates to a protein composition suitable for inducing an immune response in a vertebrate comprising 2 to 10 protein variants of a single antigen, which is the APICAL MEMBRANE ANTIGEN 1 (PfAMA1 OR AMA1) of a *Plasmodium* species. The antigen comprises a plurality of variable amino acid positions, wherein the amino acid sequences of said protein variants, in combination, represent both the frequency of occurrence of each amino acid at said variable amino acid positions and the linkage between the variable amino acid positions, and wherein said frequency of occurrence is at least between 10% to 20% such as 10%, 11%, 12%, 13%, . . . , 20% in the single antigen, and wherein at least 75% of the linkages between the variable amino acid position is presented by the combination of protein variants.

12 Claims, 11 Drawing Sheets

Fig. 2

| pos | Options | N | aa1 | freq. | aa2 | freq. | aa3 | freq. | aa4 | freq. | aa5 | freq. | aa6 | freq. | aa7 | freq. |
|---|---|---|---|---|---|---|---|---|---|---|---|---|---|---|---|---|
| 121 | EK | 233 | E | 0,987 | K | 0,013 | | | | | | | | | | |
| 162 | NK | 354 | N | 0,771 | K | 0,229 | | | | | | | | | | |
| 167 | TK | 354 | T | 0,737 | K | 0,263 | | | | | | | | | | |
| 172 | GE | 355 | G | 0,454 | E | 0,546 | | | | | | | | | | |
| 173 | NKE | 355 | N | 0,856 | K | 0,138 | E | 0,006 | | | | | | | | |
| 175 | DY | 355 | D | 0,899 | Y | 0,101 | | | | | | | | | | |
| 187 | NKE | 355 | N | 0,389 | K | 0,239 | E | 0,372 | | | | | | | | |
| 189 | LHP | 355 | L | 0,918 | H | 0,014 | P | 0,068 | | | | | | | | |
| 190 | MI | 355 | M | 0,673 | I | 0,327 | | | | | | | | | | |
| 196 | ND | 355 | N | 0,254 | D | 0,744 | | | | | | | | | | |
| 197 | GHDQRVE | 355 | G | 0,239 | H | 0,073 | D | 0,237 | Q | 0,327 | R | 0,020 | V | 0,017 | E | 0,087 |
| 199 | RK | 355 | R | 0,989 | K | 0,011 | | | | | | | | | | |
| 200 | DHLR | 354 | D | 0,446 | H | 0,404 | L | 0,073 | R | 0,076 | | | | | | |
| 201 | FLS | 355 | F | 0,789 | L | 0,186 | | | S | 0,023 | | | | | | |
| 204 | ND | 355 | N | 0,423 | D | 0,577 | | | | | | | | | | |
| 206 | EK | 355 | E | 0,783 | K | 0,217 | | | | | | | | | | |
| 207 | YD | 355 | Y | 0,837 | D | 0,163 | | | | | | | | | | |
| 224 | MI | 355 | M | 0,986 | I | 0,014 | | | | | | | | | | |
| 225 | NI | 355 | N | 0,685 | I | 0,315 | | | | | | | | | | |
| 228 | NK | 355 | N | 0,969 | K | 0,028 | | | | | | | | | | |
| 230 | EKQ | 355 | E | 0,273 | K | 0,670 | Q | 0,056 | | | | | | | | |
| 242 | DY | 355 | D | 0,485 | Y | 0,515 | | | | | | | | | | |
| 243 | KNE | 355 | K | 0,625 | N | 0,203 | E | 0,172 | | | | | | | | |
| 244 | DYN | 355 | D | 0,921 | Y | 0,039 | N | 0,039 | | | | | | | | |
| 245 | KN | 355 | K | 0,921 | N | 0,079 | | | | | | | | | | |
| 267 | QE | 355 | Q | 0,394 | E | 0,606 | | | | | | | | | | |
| 269 | KI | 355 | K | 0,958 | I | 0,042 | | | | | | | | | | |
| 282 | KI | 354 | K | 0,672 | I | 0,328 | | | | | | | | | | |
| 283 | SL | 354 | S | 0,701 | L | 0,299 | | | | | | | | | | |
| 285 | QE | 354 | Q | 0,788 | E | 0,212 | | | | | | | | | | |
| 296 | DH | 351 | D | 0,801 | H | 0,199 | | | | | | | | | | |
| 300 | KE | 345 | K | 0,725 | E | 0,275 | | | | | | | | | | |
| 308 | EQ | 167 | E | 0,641 | Q | 0,353 | | | | | | | | | | |
| 325 | HD | 166 | H | 0,976 | D | 0,018 | | | | | | | | | | |
| 330 | SP | 167 | S | 0,910 | P | 0,090 | | | | | | | | | | |
| 332 | NI | 166 | N | 0,825 | I | 0,175 | | | | | | | | | | |
| 393 | HR | 167 | H | 0,689 | R | 0,305 | | | | | | | | | | |
| 395 | KR | 165 | K | 0,921 | R | 0,079 | | | | | | | | | | |
| 404 | RT | 166 | R | 0,572 | T | 0,428 | | | | | | | | | | |
| 405 | KE | 167 | K | 0,509 | E | 0,491 | | | | | | | | | | |
| 407 | QH | 167 | Q | 0,844 | H | 0,156 | | | | | | | | | | |
| 435 | INT | 167 | I | 0,784 | N | 0,204 | T | 0,012 | | | | | | | | |
| 439 | HND | 166 | H | 0,590 | N | 0,386 | D | 0,024 | | | | | | | | |
| 448 | DN | 167 | D | 0,814 | N | 0,186 | | | | | | | | | | |
| 451 | KM | 167 | K | 0,587 | M | 0,413 | | | | | | | | | | |
| 485 | IK | 167 | I | 0,419 | K | 0,581 | | | | | | | | | | |
| 493 | AD | 167 | A | 0,216 | D | 0,784 | | | | | | | | | | |
| 496 | MI | 167 | M | 0,437 | I | 0,563 | | | | | | | | | | |
| 503 | RN | 167 | R | 0,413 | N | 0,581 | | | | | | | | | | |
| 505 | FY | 166 | F | 0,958 | Y | 0,042 | | | | | | | | | | |
| 512 | RK | 167 | R | 0,473 | K | 0,527 | | | | | | | | | | |
| 544 | KN | 143 | K | 0,664 | N | 0,336 | | | | | | | | | | |

Fig. 3

| Restricting Position | | | | Restricted position and consensus residue | | | | | | | | | | | | | | | | | | | | |
|---|---|---|---|---|---|---|---|---|---|---|---|---|---|---|---|---|---|---|---|---|---|---|---|---|
| | | | | 162 | 167 | 172 | 173 | 175 | 187 | 190 | 196 | 200 | 201 | 204 | 206 | 207 | 225 | 230 | 242 | 282 | 283 | 296 | 407 | 435 | 448 | 496 | 503 |
| Position | Freq | Options | DiCo | N | T | E | N | D | N | M | D | D | F | D | E | Y | N | K | Y | K | S | D | Q | I | D | I | N |
| 167 | 0.74 | T | 1&3 | | | | | | | | | | | | | | | | | | | | | | | | | |
| | 0.26 | K | 2 | N | | | | | | | | | | | | | | | | | | | | | | | | |
| 172 | 0.55 | E | 1&3 | | | | | | | | | | | | | | | | | | | | | | | | | |
| | 0.45 | G | 2 | N | | | | | | | | | | | | | | | | | | | | | | | | |
| 173 | 0.86 | N | 1,2&3 | | | | | | | | | | | | | | | | | | | | | | | | | |
| | 0.14 | K | | N | | | | | | | | | | | | | | | | | | | | | | | | |
| 175 | 0.90 | D | 1,2&3 | | | | | | | | | | | | | | | | | | | | | | | | | |
| | 0.10 | Y | | | | | N | | | | | | | | | | | | | | | | | | | | | |
| 187 | 0.39 | N | 2 | | | | | | | | | | | | | | | | | | | | | | | | | |
| | 0.37 | E | 3 | | | | N | | | | | | | | | | | | | | | | | | | | | |
| | 0.24 | K | 1 | N | T | E | N | D | | | | | | | | | | | | | | | | | | | | |
| 197 | 0.33 | Q | 1 | | | | | | D | | D | | | | | | | | | | | | | | | | | | |
| | 0.24 | G | 2 | | | | | | | | N* | | | | | | | | | | | | | | | | | | |
| | 0.24 | D | 3 | | | | | | | | D* | | | | | | | | | | | | | | | | | | |
| 200 | 0.45 | D | 2&3 | | | | | | | | | | | | | | | | | | | | | | | | | |
| | 0.41 | H | 1 | | | T* | | | | | D | | | | | | | | | | | | | | | | | | |
| 206 | 0.78 | E | 1&2 | | | | | | | | | | | | | | | | | | | | | | | | | |
| | 0.22 | K | 3 | | T | | N | | | M | D | H | F | D | | | | | | | | | | | | | | |
| 207 | 0.84 | Y | 1,2&3 | | | | | | | | | | | | | | | | | | | | | | | | | |
| | 0.16 | D | | | | | | | | | | | | | E | | | | | | | | | | | | | |
| 225 | 0.68 | N | 1&2 | | | | | | | | | | | | | | | | | | | | | | | | | |
| | 0.32 | I | 3 | | T* | | | | | | D* | | | D | | | | | | | | | | | | | | |
| 230 | 0.67 | K | 1&3 | | | | | | | | | | | | | | | | | | | | | | | | | |
| | 0.27 | E | 2 | | | | | D | | | | | | | E | | N | | | | | | | | | | | |
| | 0.06 | Q | | N | | | N | D | E | I | D | D | F | N | E | Y | N | | | | | | | | | | | |
| 243 | 0.63 | K | 1 | | | | | | | | | | | | | | | | | | | | | | | | | |
| | 0.20 | N | 2 | | | | N | | | | | | | | E* | | N | K* | Y | | | | | | | | | |
| | 0.17 | E | 3 | | | | N | D | | | | | | | | | | | Y | | | | | | | | | |
| 282 | 0.67 | K | 1&2 | | | | | | | | | | | | | | | | | | | | | | | | | |
| | 0.33 | I | 3 | | | | | | | | | | | | | | | | Y | | | | | | | | | |
| 283 | 0.70 | S | 1&3 | | | | | | | | | | | | | | | | | | | | | | | | | |
| | 0.30 | L | 2 | | | | | | | | | | | | | | | | | | K | | | | | | | |
| 285 | 0.79 | Q | 1&3 | | | | | | | | | | | | | | | | | | | | | | | | | |
| | 0.21 | E | 2 | | | | N* | | | | | | | | | | | | | | K | L | | | | | | |
| 296 | 0.80 | D | 1&3 | | | | | | | | | | | | | | | | | | | | | | | | | |
| | 0.20 | H | 2 | N | | | | | | | | | | | E* | | | | | | | | | | | | | |
| 332 | 0.83 | N | 1&2 | | | | | | | | | | | | | | | | | | | | | | | | | |
| | 0.17 | I | 3 | | | | N | | | | D | | | | | | | | | | | | | | | | | |
| 435 | 0.78 | I | 1&2 | | | | | | | | | | | | | | | | | | | | | | | | | |
| | 0.20 | N | 3 | | | | | | | | | | | | | | | | | | | | Q | | | | | |
| 448 | 0.81 | D | 1&3 | | | | | | | | | | | | | | | | | | | | | | | | | |
| | 0.19 | N | 2 | | | | | | | | | | | | | | | | | | | D | | I | | | | |
| 451 | 0.59 | K | 1&3 | | | | | | | | | | | | | | | | | | | | | | | | D | | |
| | 0.41 | M | 2 | | | | | | | | | | | | | | | | | | | | | | | | | |
| 503 | 0.58 | N | 1&3 | | | | | | | | | | | | | | | | | | | | | | | | | |
| | 0.41 | R | 2 | | | | | | | | | | | | | | | | | | | | | | | | | M | |
| 512 | 0.53 | K | 1&3 | | | | | | | | | | | | | | | | | | | | | | | | | | N* |
| | 0.47 | R | 2 | | | | | | | | | | | | | | | | | | | | | | | | | | |
| | | DiCo 1 | | N | T | E | N | D | K | M | D | H | F | D | E | Y | N | K | D | K | S | D | Q | I | D | I | N |
| | | DiCo 2 | | N | K | G | N | D | N | I | N | D | F | N | E | Y | N | E | Y | K | L | H | Q | I | N | M | R |
| | | DiCo 3 | | K | T | E | N | D | E | M | D | D | L | D | K | Y | I | K | Y | I | S | D | Q | N | D | I | N |

Fig. 4

|  |  |  |  | Restricted position and consensus residue | | | | | | | | | | | | | | | | | | | |
|---|---|---|---|---|---|---|---|---|---|---|---|---|---|---|---|---|---|---|---|---|---|---|---|---|
| Restricting Position | | | | 167 | 172 | 173 | 175 | 187 | 190 | 196 | 200 | 204 | 206 | 207 | 225 | 230 | 243 | 283 | 285 | 296 | 308 | 332 | 407 | 448 | 451 | 485 |
| Position | Frequency | Options | DiCo | T | E | N | D | N | M | D | D | D | E | Y | N | K | K | S | Q | D | E | N | Q | D | K | K |
| 162 | 0.77 | N | 1&2 | | | | | | | | | | | | | | | | | | | | | | | |
|  | 0.23 | K | 3 | T | E | N | D* | | | | | | | | | | | | | D | | | | | | |
| 167 | 0.74 | T | 1&3 | | | | | | | | | | | | | | | | | | | | | | | |
|  | 0.26 | K | 2 | | G | | D* | | | | | | E | Y* | N* | | | | | | | | | | | |
| 172 | 0.55 | E | 1&3 | | | | D* | | | | | | | | | | | | | | | | | | | |
|  | 0.45 | G | 2 | | | | | | | | | | | | | | | | | | | | | | | |
| 173 | 0.86 | N | 1,2&3 | | | | | | | | | | | | | | | | | | | | | | | |
|  | 0.14 | K | | | | | D | N | | | | | E | | | | | | | | | N | | | | |
| 187 | 0.39 | N | 2 | | | | | | | | | | | | | | | | | | | | | | | |
|  | 0.37 | E | 3 | | | | | | | | | | | | | | | | | | | | | | | |
|  | 0.24 | K | 1 | | | | | | M* | D* | | | | | | | | | | | | | | | | |
| 190 | 0.67 | M | 1&3 | | | | | | | | | | | | | | | | | | | | | | | |
|  | 0.33 | I | 2 | | | | | | | | | | E | | N* | | | | | | | | | | | |
| 196 | 0.74 | D | 1&3 | | | | | | | | | | | | | | | | | | | | | | | |
|  | 0.25 | N | 2 | | | | | | | | D | | E | | N | | | | | | | | N | | | |
| 197 | 0.33 | Q | 1 | | | | | | | | | | | | | | | | | | | | | | | |
|  | 0.24 | G | 2 | | | | | | | | D | | E | | N | | | | | | | N | | | | |
|  | 0.24 | D | 3 | | | | | | | | | | E | | | | | | | | | N | | | | |
| 200 | 0.45 | D | 2&3 | | | | | | | | | | E | | N* | | | | | | | | | | | |
|  | 0.41 | H | 1 | | | | | | | | | D | | | | | | | | | | | | | | |
| 201 | 0.79 | F | 1&2 | | | | | | | | | | | | | | | | | | | | | | | |
|  | 0.19 | L | 3 | | | | | | | | | | E | | | | | | | | | N | | | | |
| 204 | 0.58 | D | 1&3 | | | | | | | | | | | | | | | | | | | | | | | |
|  | 0.42 | N | 2 | | | | | | | | | | E | | N | | | | | | | | | | | |
| 206 | 0.78 | E | 1&2 | | | | | | | | | | | | | | | | | | | | | | | |
|  | 0.22 | K | 3 | | | | | | | | | | | Y | | K | | | | D* | | | | | | |
| 225 | 0.68 | N | 1&2 | | | | | | | | | | | | | | | | | | | | | | | |
|  | 0.32 | I | 3 | | | | | | | | | | | | | K | | | | | | | | | | |
| 242 | 0.51 | Y | 2&3 | | | | | | | | | | | | | | | | | | | | | | | |
|  | 0.49 | D | 1 | | | | | | | | | | | | | | K | | | | | | | | | |
| 243 | 0.63 | K | 1 | | | | | | | | | | | | | | | | | | | | | | | |
|  | 0.20 | N | 2 | | | | | | | | | | | | | | | | | | E | N | | | | |
|  | 0.17 | E | 3 | | | | | | | | | | | | | | | | | | | | | | | |
| 282 | 0.67 | K | 1&2 | | | | | | | | | | | | | | | | | | | | | | | |
|  | 0.33 | I | 3 | | | | | | | | | | | | | | | S | Q | | | | | | | |
| 283 | 0.70 | S | 1&3 | | | | | | | | | | | | | | | | | Q | | | | | | |
|  | 0.30 | L | 2 | | | | | | | | | | | | | | | | | | | | | | | |
| 296 | 0.80 | D | 1&3 | | | | | | | | | | | | | | | | | | | | | | | |
|  | 0.20 | H | 2 | | | | | | | | | | | | | | | | | | | | | | D | |
| 332 | 0.83 | N | 1&2 | | | | | | | | | | | | | | | | | | | | | | | |
|  | 0.17 | I | 3 | | | | | | | | | | | | | | | | | | | | Q | | | |
| 435 | 0.78 | I | 1&2 | | | | | | | | | | | | | | | | | | | | | | | |
|  | 0.20 | N | 3 | | | | | | | | | | | | | | | | | | | | | D | K | |
| 448 | 0.81 | D | 1&3 | | | | | | | | | | | | | | | | | | | | | | | |
|  | 0.19 | N | 2 | | | | | | | | | | | | | | | | | | | | | | M | K |
| 451 | 0.59 | K | 1&3 | | | | | | | | | | | | | | | | | | | | | | | |
|  | 0.41 | M | 2 | | | | | | | | | | | | | | | | | | | | | | | K |
| | | DiCo 1 | | T | E | N | D | K | M | D | H | D | E | Y | N | K | K | S | Q | D | E | N | Q | D | K | K |
| | | DiCo 2 | | K | G | N | D | N | I | N | D | N | E | Y | N | E | N | L | E | H | E | N | Q | N | M | K |
| | | DiCo 3 | | T | E | N | D | E | M | D | D | D | K | Y | I | K | E | S | Q | D | Q | I | Q | D | K | I |

Fig. 5

```
SEQ ID NO: 29   97   IEIVERSNYMGNPWTEYMAKYDIE 120
SEQ ID NO: 1    97   IEIVERSNYMGNPWTEYMAKYDIE 120
SEQ ID NO: 30   97   IEIVERSNYMGNPWTEYMAKYDIE 120
SEQ ID NO: 2    97   IEIVERSNYMGNPWTEYMAKYDIE 120
SEQ ID NO: 3    97   IEIVERSNYMGNPWTEYMAKYDIE 120
SEQ ID NO: 31   97   IEIVERSNYMGNPWTEYMAKYDIE 120
SEQ ID NO: 25   97   IEIVERSNYMGNPWTEYMAKYDIE 120

SEQ ID NO: 29   EVHGSGIRVDLGEDAEVAGTQYRLPSGKCPVFGKGIIIENSKTTFLTPVATGNQYLKDGG
SEQ ID NO: 1    EVHGSGIRVDLGEDAEVAGTQYRLPSGKCPVFGKGIIIENSQTTFLTPVATENQDLKDGG180
SEQ ID NO: 30   KVHGSGIRVDLGEDAEVAGTQYRLPSGKCPVFGKGIIIENSKTTFLTPVATENQDLKDGG
SEQ ID NO: 2    EVHGSGIRVDLGEDAEVAGTQYRLPSGKCPVFGKGIIIENSQTTFLKPVATGNQDLKDGG
SEQ ID NO: 3    EVHGSGIRVDLGEDAEVAGTQYRLPSGKCPVFGKGIIIENSKTTFLTPVATENQDLKDGG
SEQ ID NO: 31   EVHGSGIRVDLGEDAEVAGTQYRLPSGKCPVFGKGIIIENSKTTFLKPVATGNQDLKDGG
SEQ ID NO: 25   EVHGSGIRVDLGEDAEVAGTQYRLPSGKCPVFGKGIIENSNTTFLTPVATENQDLKDGG

SEQ ID NO: 29   FAFPPTEPLMSPMTLDEMRHFYKDNKYVKNLDELTLCSRHAGNMIPDNDKNSNYKYPAVY
SEQ ID NO: 1    FAFPPTKPLMSPMTLDQMRHFYKDNEYVKNLDELTLCSRHAGNMNPDNDKNSNYKYPAVY240
SEQ ID NO: 30   FAFPPTEPLISPMTLDQMRHLYKDNEYVKNLDELTLCSRHAGNMNPDNDKNSNYKYPAVY
SEQ ID NO: 2    FAFPPTNPLISPMTLNGMRDFYKNNEYVKNLDELTLCSRHAGNMNPDNDENSNYKYPAVY
SEQ ID NO: 3    FAFPPTEPLMSPMTLDDMRDLYKDNKYVKNLDELTLCSRHAGNMIPDNDKNSNYKYPAVY
SEQ ID NO: 31   FAFPPTNPLISPMTLNGMRDFYKNNEYVKNLDELTLCSRHAGNMNPDNDKNSNYKYPAVY
SEQ ID NO: 25   FAFPPTNPLMSPMTLDQMRDFYKDNEYVKNLDELTLCSRHAGNMNPDNDKNSNYKYPAVY

SEQ ID NO: 29   DDKDKKCHILYIAAQENNGPRYCNKDESKRNSMFCFRPAKDISFQNYVYLSKNVVDNWEK
SEQ ID NO: 1    DDKDKKCHILYIAAQENNGPRYCNKDESKRNSMFCFRPAKDKSFQNYVYLSKNVVDNWEK300
SEQ ID NO: 30   DYEDKKCHILYIAAQENNGPRYCNKDESKRNSMFCFRPAKDKLFENYVYLSKNVVDNWEE
SEQ ID NO: 2    DYNDKKCHILYIAAQENNGPRYCNKDESKRNSMFCFRPAKDKLFENYVYLSKNVVHNWEE
SEQ ID NO: 3    DYEDKKCHILYIAAQENNGPRYCNKDQSKRNSMFCFRPAKDISFQNYVYLSKNVVDNWEK
SEQ ID NO: 31   DYNDKKCHILYIAAQENNGPRYCNKDQSKRNSMFCFRPAKDKLFENYVYLSKNVVDNWEE
SEQ ID NO: 25   DYKDKKCHILYIAAQENNGPRYCNKDESKRNSMFCFRPAKDKSFQNYTYLSKNVVDNWEK

SEQ ID NO: 29   VCPRKNLQNAKFGLWVDGNCEDIPHVNEFPAIDLFECNKLVFELSASDQPKQYEQHLTDY
SEQ ID NO: 1    VCPRKNLENAKFGLWVDGNCEDIPHVNEFSANDLFECNKLVFELSASDQPKQYEQHLTDY360
SEQ ID NO: 30   VCPRKNLENAKFGLWVDGNCEDIPHVNEFSANDLFECNKLVFELSASDQPKQYEQHLTDY
SEQ ID NO: 2    VCPRKNLENAKFGLWVDGNCEDIPHVNEFSANDLFECNKLVFELSASDQPKQYEQHLTDY
SEQ ID NO: 3    VCPRKNLQNAKFGLWVDGNCEDIPHVNEFSAIDLFECNKLVFELSASDQPKQYEQHLTDY
SEQ ID NO: 31   VCPRKNLENAKFGLWVDGNCEDIPHVNEFSANDLFECNKLVFELSASDQPKQYEQHLTDY
SEQ ID NO: 25   VCPRKNLENAKFGLWVDGNCEDIPHVNEFSANDLFECNKLVFELSASDQPKQYEQHLTDY

SEQ ID NO: 29   EKIKEGFKNKNADMIKSAFLPTGAFKADRYKSHGKGYNWGNYNTETQKCEIFNVKPTCLI
SEQ ID NO: 1    EKIKEGFKNKNADMIKSAFLPTGAFKADRYKSHGKGYNWGNYNRKTQKCEIFNVKPTCLI420
SEQ ID NO: 30   EKIKEGFKNKNADMIKSAFLPTGAFKADRYKSRGKGYNWGNYNTETQKCEIFNVKPTCLI
SEQ ID NO: 2    EKIKEGFKNKNADMIKSAFLPTGAFKADRYKSRGKGYNWGNYNRKTQKCEIFNVKPTCLI
SEQ ID NO: 3    EKIKEGFKNKNADMIKSAFLPTGAFKADRYKSHGKGYNWGNYNTETQKCEIFNVKPTCLI
SEQ ID NO: 31   EKIKEGFKNKNADMIKSAFLPTGAFKADRYKSHGKGYNWGNYNRETQKCEIFNVKPTCLI
SEQ ID NO: 25   EKIKEGFKNKNASMIKSAFLPTGAFKADRYKSHGKGYNWGNYNRKTQKCEIFNVKPTCLI
```

Fig. 5 (continued)

```
SEQ ID NO: 29    NDKSYIATTALSHPIEVENNFPCSLYKDEIMKEIERESKRIKLNDNDDEGNKKIIAPRIF
SEQ ID NO: 1     NDKSYIATTALSHPIEVEHNFPCSLYKDEIKKEIERESKRIKLNDNDDEGNKKIIAPRIF480
SEQ ID NO: 30    NDKSYIATTALSHPNEVENNFPCSLYKDEIKKEIERESKRIKLNDNDDEGNKKIIAPRIF
SEQ ID NO: 2     NDKSYIATTALSHPIEVENNFPCSLYKNEIMKEIERESKRIKLNDNDDEGNKKIIAPRIF
SEQ ID NO: 3     NDKSYIATTALSHPNEVEHNFPCSLYKDEIKKEIERESKRIKLNDNDDEGNKKIIAPRIF
SEQ ID NO: 31    NDKSYIATTALSHPIEVEHNFPCSLYKDEIKKEIERESKRIKLNDNDDEGNKKIIAPRIF
SEQ ID NO: 25    NNSSYIATTALSHPIEVEHNFPCSLYKDEIKKEIERESKRIKLNDNDDEGNKKIIAPRIF

SEQ ID NO: 29    ISDDKDSLKCPCDPEMVSQSTCRFFVCKCVERRAEVTSNNEVVVKEEYKDEYADIPEHKPTYDKM
SEQ ID NO: 1     ISDDKDSLKCPCDPEIVSQSTCNFFVCKCVEKRAEVTSNNEVVVKEEYKDEYADIPEHKPTYDKM545
SEQ ID NO: 30    ISDDKDSLKCPCDPEIVSQSTCNFFVCKCVEKRAEVTSNNEVVVKEEYKDEYADIPEHKPTYDKM
SEQ ID NO: 2     ISDDKDSLKCPCDPEMVSQSTCRFFVCKCVERRAEVTSNNEVVVKEEYKDEYADIPEHKPTYDNM
SEQ ID NO: 3     ISDDIDSLKCPCAPEIVSQSTCNFFVCKCVEKRAEVTSNNEVVVKEEYKDEYADIPEHKPTYDKM
SEQ ID NO: 31    ISDDKDSLKCPCDPEMVSQSTCRFFVCKCVERRAEVTSNNEVVVKEEYKDEYADIPEHKPTYDKM
SEQ ID NO: 25    ISDDKDSLKCPCDPEIVSNSTCNFFVCKCVEKRAEVTSNNEVVVKEEYKDEYADIPEHKPTYDKM
```

Fig. 6

|       | Cons.      | FVO        | 3D7        | HB3        | DiCo1      | DiCo2       | DiCo3 |
|-------|------------|------------|------------|------------|------------|-------------|-------|
| Cons. | -          | 17         | 20         | 16         | 4          | 21          | 16    |
| FVO   | 12 - 1 - 4 | -          | 24         | 18         | 20         | 9           | 25    |
| 3D7   | 11 - 4 - 5 | 18 - 3 - 3 | -          | 24         | 18         | 27          | 17    |
| HB3   | 10 - 3 - 3 | 11 - 2 - 5 | 15 - 3 - 6 | -          | 16         | 21          | 18    |
| DiCo1 | 4 - 0 - 0  | 15 - 1 - 4 | 9 - 4 - 5  | 10 - 3 - 3 | -          | 23          | 18    |
| DiCo2 | 13 - 1 - 7 | 4 - 2 - 3  | 20 - 5 - 2 | 13 - 2 - 6 | 15 - 1 - 7 | -           | 34    |
| DiCo3 | 10 - 3 - 3 | 16 - 2 - 7 | 8 - 1 - 8  | 12 - 2 - 4 | 12 - 3 - 3 | 20 - 4 - 10 | -     |

Legend, symbols refer to single rabbits. Within each treatment group, same symbols represent the same animals. Circles rabbit 1, crosses rabbit 2, triangles rabbit 3, squares rabbit 4 and diamonds rabbit 5.

Legend, symbols refer to single rabbits. Within each treatment group, same symbols represent the same animals. circles rabbit 1, crosses rabbit 2, triangles rabbit 3, squares rabbit 4 and diamonds rabbit 5.

Legend: open circles DiCo mix, crosses DiCo 1, triangles DiCo 2, squares DiCo3 and diamonds FVO-AMA-1.

US 8,741,305 B2

PROTEIN COMPOSITION FOR INDUCING AN IMMUNE RESPONSE IN A VERTEBRATE COMPRISING A PLURALITY OF PROTEIN VARIANTS COVERING THE HETEROGENEITY OF A SINGLE ANTIGEN, AMA1

FIELD OF THE INVENTION

The present invention relates to a protein composition for inducing an immune response in a vertebrate comprising a plurality of protein variants covering the heterogeneity of a single antigen. The present invention further relates to the protein variants itself, nucleic acids encoding the protein variants, and expression vectors and host cells for producing the protein variants according to the present invention. The protein composition according to the present invention is especially suitable for providing an immune response against the malaria causing infectious agent *Plasmodium*, such as *Plasmodium falciparum*.

BACKGROUND OF THE INVENTION

In a relatively large number of cases, an infectious agent, such as *Plasmodium* or influenza, escapes a previous acquired (protective) immune response by changing one or more of its immune response inducing agents. Because of this, a previous acquired (protective) immune response, for example through vaccination or a previous infection, would be no longer suffice to control the establishment of the infectious agent.

In a number of cases, the (protective) immune response inducing agents, or antigens, are one or more surface proteins of the infectious agent and the changes involve amino acid substitution in these surface proteins. Such substituted proteins can be referred to as protein variants or polymorphic proteins of the immune response inducing agent or antigen.

The amino acid substitutions are in general limited to a specific subset of amino acid positions, because biological function(s) of the (protective) immune response inducing protein. For example, if the biological function of the (protective) immune response inducing protein is attachment to the outer wall of a host cell, the subset of amino acid positions which can be substituted in order to escape the immune system of the host is limited to those amino acid positions not affecting the attachment.

Further, because of the associated biological function(s), the number of possible amino acid substitutions at a specific amino acid position is limited.

For example, substitution of an acidic amino acid, such as aspartic acid (Asp), for a polar amino acid, such as serine (Ser), could affect the function of the immune response inducing protein and could therefore be not a suitable amino acid substitution for the infectious agent to escape the immune system of the host.

Furthermore, there appears to be a linkage, or correlation, between certain specific amino acid substitutions at specific positions of the antigen. In other words, the presence of, for example, an alanine (Ala) at a certain position in the antigen can be linked or correlated with the presence of, for example, a glycine (Gly) at a nearby or remote amino acid position in the antigen.

However, although the number of possible amino acid substitutions in a (protective) immune response inducing protein is limited, the number of possible variants of this protein remains still very high.

An example of this is the immunogenic hemagglutinin (HA) surface glycoprotein of the viral infectious agent influenza. The possible substitutable amino acid positions in this glycoprotein are so high that each year the most prevalent (regional) protein variants of HA have to be selected to provide an effective influenza vaccine for only that year.

Another example is the PfAMA-1 protein of the malaria causing infectious agent *Plasmodium falciparum*.

Malaria is estimated to cause up to 500 million clinical cases and 2 million deaths annually. Most of the severe morbidity and mortality occurs through infection with *Plasmodium falciparum* in young children and pregnant women of sub-Saharan Africa.

Several potential (protective) immune response inducing agents have been identified for vaccine development, one of these being *Plasmodium falciparum* Apical Membrane Antigen 1 (PfAMA1 or AMA1), encoded by a single copy gene.

Evidence from rodent and non-human primate malaria models shows that antibody responses to AMA1 can reduce levels of infection and that antibodies to AMA1 inhibit asexual parasite multiplication in vitro.

In endemic areas the immune system generates anti-AMA1 antibodies in response to infection and these may correlate with protection.

AMA-1 (FIG. 1) is an 83 kDa protein comprising a large N-terminal ectodomain, a transmembrane region and a approximately 50 amino acid C-terminal cytoplasmic tail. The ectodomain contains 16 conserved cysteine residues that form eight intramolecular disulphide bonds defining a potential three domain structure. Recent crystal structures for AMA1 confirms this three domain structure, but suggests there is considerable interaction between the domains.

Antibodies to AMA1 block merozoite invasion of erythrocytes, merozoite reorientation at the erythrocyte surface, block proteolytic processing, and asexual blood stage parasites devoid of AMA1 appear not to be viable, suggesting that AMA1 provides a critical and non-redundant biological function during erythrocyte invasion.

AMA1 is also present on sporozoite stages of development suggesting vaccination with AMA1 may target more than just asexual erythrocytic development.

However, similar to hemagglutinin (HA) of influenza, AMA1 is known to be liable to amino acid substitutions providing an escape from an earlier acquired (protective) immune response.

This is exemplified by immunization studies in rabbits showing that, although antibodies obtained to PfAMA1 from one strain of malaria inhibit the growth of the homologous strain well, other strains are inhibited to a variably lesser degree. This suggests that PfAMA1 amino acid substitutions or polymorphism may diminish the efficacy of PfAMA1 based vaccines.

An rather obvious vaccine strategy against an infectious agent, such as influenza or *Plasmodium*, would be to include all known, or even all theoretically possible, protein variants or polymorphic forms of an antigen in one vaccine preparation in order to induce an effective (protective) immune response against all known, and even future, variants or polymorphs of the infectious agent.

However, such vaccine strategy would be rather unpractical or even impossible because of the large number of protein variants or polymorphic forms involved. Only for *Plasmodium falciparum*, already more than 300 different protein variants or polymorphic forms of the AMA1 protein are known. As a consequence, a vaccine preparation effective against only the known *Plasmodium falciparum* polymorphs would already comprise more than 300 protein variants.

Such vaccine preparations are not only difficult, laborious, and expensive to produce, even using the present days recombinant DNA technologies, their therapeutic effectiveness in inducing an immune response would also be questionable. When presented in a single vaccine preparation to the immune system, some protein variants, or parts thereof, would inherently be more immunogenic thereby inhibiting, or even preventing, the development of an immune response against less immunogenic protein variant or parts thereof.

Further, such vaccine preparation, comprising all known variants of an antigen, would probably not be effective against future strains of the infectious agent which are likely to develop because of the evolutionary pressure of such vaccine preparation.

SUMMARY OF THE INVENTION

Therefore, it is an objective of the present invention to provide a protein composition or vaccine preparation suitable for inducing a (protective) immune response in a vertebrate against an infectious agent obviating the above drawbacks.

It is a further objective of the present invention to provide a protein composition or vaccine preparation suitable for inducing a (protective) immune response in a vertebrate effective against polymorphic antigens (of infectious agents).

Still a further objective of the present invention is to provide a protein composition or vaccine preparation which can be relatively easy to produce.

Still another object of the present invention is to provide a protein composition or vaccine preparation which is relatively cheap and therefore economically feasible.

These objects and other objects and advantages of the present invention are met by a protein composition as defined in the appended claims.

Specifically, the above objects and other objects and advantages of the present invention are met by a protein composition suitable for inducing an immune response in a vertebrate comprising 2 to 20 protein variants of a single antigen wherein the antigen comprises a plurality of variable amino acid positions, wherein the amino acid sequences of said protein variants, in combination, represent both the frequency of occurrence of each amino acid at said variable amino said variable amino acid positions and the linkage between the variable amino acid positions, and wherein said frequency of occurrence is at least 10 to 20% in the single antigen, and wherein at least 75% of the linkages between the variable amino acid positions is presented by the combination of protein variants.

Using the above defined protein variants, the present inventors have surprisingly discovered that a single vaccine preparation can be provided effective against known and, possibly, future (highly) polymorphic infectious agents.

Because of the relatively small number, i.e., 2 to 10, of protein variants, such protein composition or vaccine preparation will be easier to produce and more costs effective compared to a protein composition or vaccine preparation comprising all known naturally occurring protein variants of a polymorphic infectious agent.

Further, the relatively small number, i.e., 2 to 10, protein variants will reduce, or even eliminate, any immunogenic dominance of certain protein variants or parts thereof.

According to the present invention, the antigen comprises a plurality of variable amino acid positions. Such antigen can be any immunogenic protein of an infectious agent such as hemagglutinin of influenza or AMA1 of *Plasmodium*, as long as it comprises a number of amino acid positions which are found in nature to be variable or substituted.

Although the present invention is not particularly limited to a specific number of variable or substituted amino acid position, it logically follows that the present invention will be preferably used when the number of variable amino acid substitutions increases. This because the number of possible protein variants will also proportionally increase.

The present invention is preferably used when the number of variable amino acid substitutions is at least 10, more preferably at least 20, even more preferably at least 30, and most preferably 40 or more.

The presence and the number of variable amino acid positions in a given antigen can routinely be determined by the skilled person using standard techniques.

For example, all known naturally occurring variants of an antigen can be aligned using the maximum homology between the sequences. An amino acid position in the antigen is designated a variable position if at the corresponding positions in the known antigens more than 1 species of amino acid can be present.

For example, an alignment of 50 known species of an immunogenic protein of 500 amino acids of an infectious agent can reveal that, starting numbering from the N-terminus, amino acid positions 4, 60, 45, 57, 256, 313, 345, 456, 457, 458, 478, 498, and 497 can contain different amino acids or, in other words, the amino acid at this position can, in nature, be substituted by another amino acid.

The "frequency of occurrence" as used herein is defined as the percentage of occurrence of a species of amino acid in the naturally occurring variants. In other words, if amino acid position 45 is in 20% of the naturally occurring variants an Alanine (Ala), in 45% a Glycine (Gly), and in 35% a Valine (Val), then the frequency of occurrence for position 45 is 20% Ala, 45% Gly, and 35% Val.

The "linkage between the variable amino acid positions", as used herein, is defined is the statistical occurrence, i.e., $p<0.05$, in a natural variant of a single amino acid or stretch of amino acids at (a) variable position (s) in combination with a single amino acid or stretch of amino acids at (an)other variable position(s). For example, the occurrence of the amino acid sequence "TEND" at variable positions 45, 46, 47, and 48 is designated "linked" if its occurrence is statistically correlated with the occurrence of the amino acid valine (Val) at position 123.

The term "in combination", as used herein is defined as the combination of all protein variants according to the present invention aligned using the maximum homology.

For example, "combined" for variable amino acid position 345 would mean that all amino acids present at this position would be taken into account. If position 345 is in 30% of the protein variants an alanine (Ala) and in 70% of the protein variants a valine (Val), then combined for this specific position would mean that the frequency of occurrence in the combined protein variants is 70% Ala and 30% Val.

With respect to the linkages, a linkage is regarded as preserved in combination if this particular linkage can be found in any of the protein variants. In other words, the linkage can be found in at least one of the protein variants.

The term "represent" as used herein is used to indicate that the frequency of occurrence of an amino acid at a specific position in nature, is reflected in the protein variants according to the present invention. This does not imply that the natural frequency of occurrence should also be found in the combination of protein variants according to the present invention.

It rather implies that if an amino acid at a certain variable position is more frequently found in nature, this more frequent occurrence should, if possible, also be reflected in the combination of protein variants according to the present invention.

For example, if in nature the amino acid valine (Val) is found in 60% of the cases, glycine (Gly) in 30% of the cases, and serine (Ser) in 10% of the cases at position 456, assuming that 6 protein variants are used for the protein composition, then Val is preferably present in 3 protein variants, Gly in 2 protein variants and Ser in 1 protein variant at this position.

In the above situation, wherein only 4 protein variants are used, then Val is preferably present in 2 protein variants, Gly in 1 protein variant and Ser in 1 protein variant at this position, reflecting the prevalence for Val at this position in the majority of cases.

The number of protein variants in a specific protein composition or vaccine preparation is dependent on the amino acid variability of the antigen or the number of known sequence variants. Such variability can dictate that at least 2, 3, 4, 5, 6, 7, 8, 9, or 10 protein variants need to be used.

According to the present invention, the relation between the number of protein variants and the variability of the antigen is determined by the variable amino acid positions in the antigen showing the largest variability, i.e., number of different amino acids.

For example, if amino acid position 258 shows the largest variability by dictating three possible amino acid substitutions at this position, then the minimal number of protein variants should be at least 3 allowing to reflect this variability in the combination of protein variants. In other words, at least 3 protein variants are needed that represent the 3 possible amino acids at this position.

If in case 60% of the cases show Val at this position and 20% of the cases show either Gly or Ser at this position, then preferably, the number of protein variants is 4 allowing 2 protein variants with Val at position 258, 1 protein variant with Cys at this position and 1 protein variant with Gly at this position.

It is surprisingly found by the present inventors that by using the frequency of occurrence and the linkage, whereby only amino acids at variable positions with a frequency of occurrence of at least 10-20%, such as at least 10, 11, 12, 13, 14, 15, 16, 17, 18, 19, or 20% are taken into account, and at least 75% such as 75, 80, 85, 90, 95, 99, 100% of the linkages found in nature are preserved in the combination of protein variants, a protein composition can be prepared which is able, using a limited number of proteins, to substantially reflect the immunogenic repertoire of a (highly) polymorphic naturally occurring protein.

According to a preferred embodiment of the present invention, the single antigen in the protein composition is the AMA1 protein of a *Plasmodium* species selected from the group consisting of falciparum, vivax, knowlesi, malariae and ovale, preferably *Plasmodium falciparum*.

As already indicated above, the number of known variants of the AMA1 protein of *Plasmodium* is already well above 300. In addition, the number of variable amino acid positions in this protein is well over 40.

Because the present invention provides a single protein composition capable of immunogenically covering, using a limited number of protein variants, such high variability, the protein composition according to the present invention is especially suited to be used for a vaccine based on the AMA1 protein.

In an especially preferred embodiment of the protein composition according to the present invention the variable amino acid positions are 162, 167, 172, 173, 175, 187, 190, 196, 197, 200, 201, 204, 206, 207, 225, 230, 242, 243, 267, 282, 283, 285, 296, 300, 308, 332, 393, 404, 405, 407, 435, 439, 448, 451, 485, 493, 496, 503, 512, or 544 of the AMA1 protein of *Plasmodium falciparum* in the protein composition.

It has been found by the present inventors that when these variable amino acid positions are taken into account when developing the protein composition according to the present invention, substantially all relevant immunogenic variants of this protein in naturally occurring variants of *Plasmodium falciparum* are covered.

The protein composition according to the present invention preferably comprises at least three protein variants selected from the group consisting of SEQ ID Nos 1 to 12, more preferably at least three protein variants selected from the group consisting of SEQ ID Nos 1 to 6 and most preferably three protein variants comprising SEQ ID No 1, SEQ ID No 2, and SEQ ID No 3.

In a particularly preferred embodiment, the protein variants of the present protein composition are linked. Such linkage can be provided either chemically or through recombinant DNA technology using standard method well known to the skilled person.

For example, separate nucleic acid sequences encoding the different protein variants can be linked by, for example PCR or ligation, using a linker nucleic acid sequence. After inserting such linked construct in a suitable expression vector, the construct encoding the linked protein variants is expressed as a single protein molecule which can be, after suitable isolation, be incorporated in the protein composition.

Because of the inventive concept of the protein composition according to the present invention, the present invention also relates to protein variants chosen from the group consisting of SEQ ID Nos 1 to 12, preferably protein variants chosen from the group consisting of SEQ ID Nos 1 to 6, and most preferably potein variant chosen from the group consisting of SEQ ID Nos 1 to 3.

Similarly, the present invention also relates to nucleic acid sequences encoding the above protein variants, preferred protein variants, and most preferred protein variants, preferably SEQ ID Nos 12 to 24, more preferably SEQ ID Nos 12 to 18, and most preferably SEQ ID Nos 12 to 14.

These nucleic acid sequences can be suitably inserted, ligated or recombined in an expression vector under the control of, and operably linked to, suitable regulation and propagation signals such as a promoter, a terminator, secretion signals, enhancer(s), origin(s) of replication, a selection marker, etc.

Hence, the present invention also relates to expression vectors comprising a DNA sequence according to the present invention, preferably pPicZalpha or pPIC9, allowing expression of the protein variants in the preferred methylotropic yeast *Pichia pastoris*.

Such expression vector is preferably transformed or transfected, although integration into the genome can also be envisaged, in a suitable host cell allowing expressing of the protein variants according to the present invention. Hence the present invention also relates to a host organism transformed or transfected with the above defined expression vectors. The host organism is preferably *Pichia pastoris*.

Because of the advantageous immunogenic properties of the protein composition according to the present invention, the invention also relates to the use of a protein composition according to the present invention for the preparation of a medicament for vaccinating a vertebrate, preferably against malaria. The vertebrate is preferably a human.

The protein composition according to the present invention can be obtained using a method for producing a protein composition, comprising:

a) determining, in an antigen, the variable amino acid positions; the frequency of occurrence of each amino acid at said variable amino acid positions; and the linkage between the variable amino acid positions;

b) determining the variable amino acid position comprising the maximal number X of different amino acids, wherein the frequency of occurrence of each different amino acid is at least 10-20%;

c) designing at least X protein variants representing, in combination, the frequency of occurrence of each amino acid at each variable position.

In a preferred embodiment, the design of the at least X protein variants further represents, in combination, at least 75% of the linkage between the variable amino acid positions.

In a particularly preferred embodiment of the method according to the present invention, step (c) comprises designing protein variants $Y_1$ to $Y_x$ by assigning to a variable amino acid position in protein variant $Y_1$ the most frequent occurring amino acid at this position and to $Y_x$ the less frequent occurring amino acid at this position, assigning to the corresponding amino acid position in protein variants $Y_2$ to $Y_{x-1}$ either the remaining amino acid(s) or the same amino acids depending on their frequency of occurrence under the proviso that the established linkage between the variable amino acid positions is preserved in at least 75% of the cases.

The present invention will be further illustrated using an example showing, in detail, a preferred embodiment thereof In the example reference is made to the appended figures.

BRIEF DESCRIPTION OF THE DRAWINGS

FIG. 2 shows a summary of the frequency of occurrence of the amino acids of the AMA1 protein of *plasmodium falciparum*. Indicated are the amino acid position, the amino acids at the position, their frequencies and the number of AMA1 sequences in which the indicated amino acid was found;

FIG. 3 shows the upstream linkages between the different variable amino acid positions from variable amino acid position 162;

FIG. 4 shows the downstream linkages between the different variable amino acid positions from variable amino acid position 162;

FIG. 5 shows alignment of DiCo1 (SEQ ID NO: 1), DiCo2 (SEQ ID NO: 2), DiCo3 (SEQ ID NO: 3) and the yeast expressed HB3-AMA1 (SEQ ID NO: 30), 3D7-AMA1 (SEQ ID NO: 29) and FVO-AMA1 (SEQ ID NO: 31), as well as the consensus sequence (SEQ ID NO: 25) that was derived from the alignment of the 356 PfAMA1 sequences obtained from the Genbank database;

FIG. 6 shows differences between *Pichia*-expressed sequences in domains 1 to 3. Upper right: total differences between alleles and lower left: differences according to domain;

DETAILED DESCRIPTION OF THE INVENTION

Figure 1:
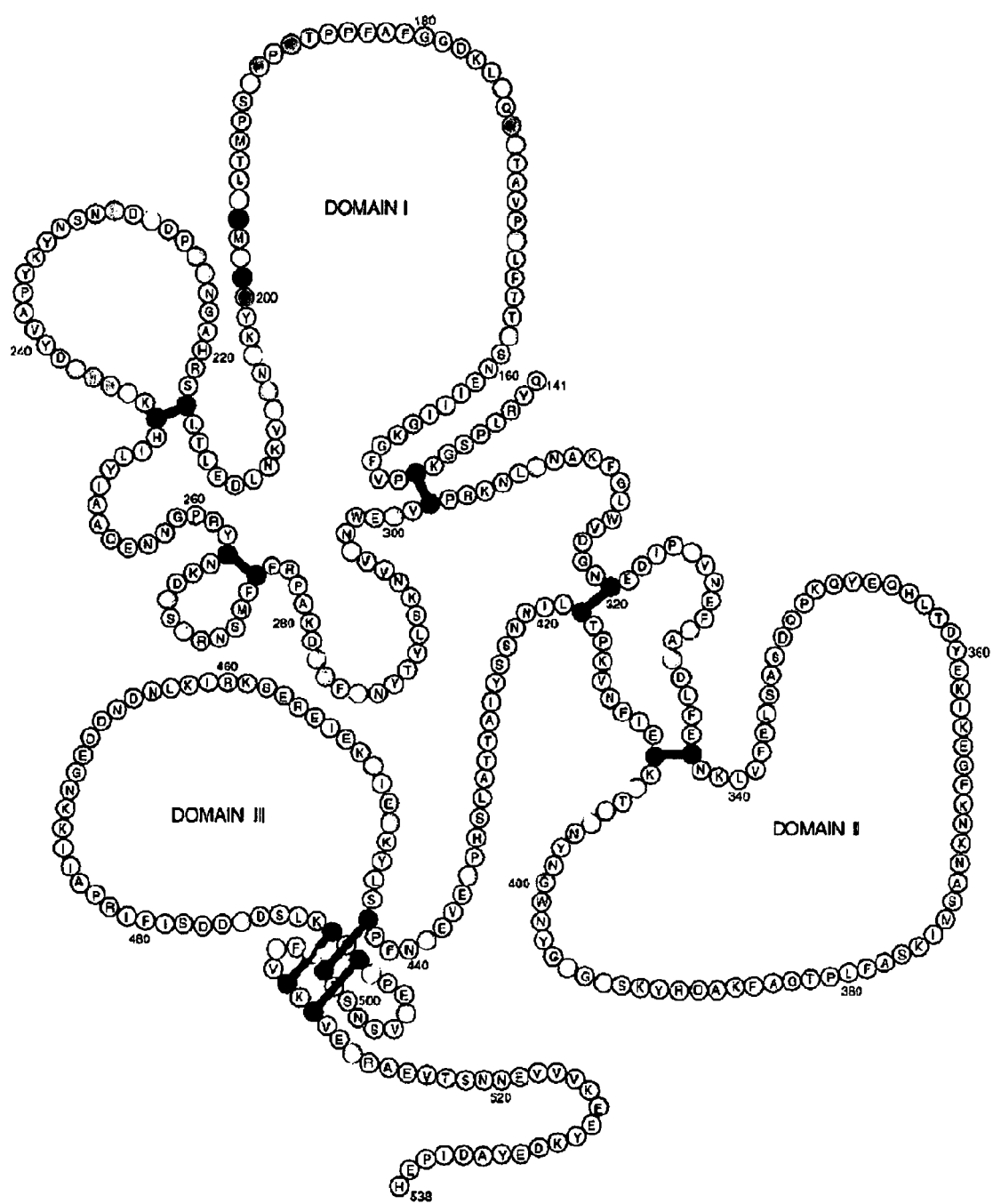
FIG. 1 is a schematic representation of the AMA1 protein of *Plasmodium falciparum*.

A Diversity-covering Approach to Immunisation with *Plasmodium falciparum* AMA1; Broader Allelic Recognition and Growth Inhibition Summary

*Plasmodium falciparum* AMA1 (PfAMA1), a candidate malaria vaccine, is polymorphic. This polymorphism is believed to be generated predominantly under immune selection pressure, and as a result may compromise attempts at vaccination.

355 PfAMA1 sequences obtained predominantly from parasites in endemic areas were aligned and analysed and it was shown that about 10% of the 622 amino acid residues have potential to vary between alleles (FIG. 2). Linkages between polymorphic residues have also been identified (FIGS. 3 and 4). From this analysis three Diversity-Covering (DiCo) PfAMA1 sequences were generated that take account of linkages and when taken together incorporate 80% of all amino acid variability. For each of the three DiCo sequences a synthetic gene was constructed and used to transform the methylothrophic yeast *Pichia pastoris*, allowing recombinant expression at yields between 50 and 100 mg/L. All three DiCo proteins were reactive with the reduction sensitive monoclonal antibody 4G2, indicating that the DiCo's had a similar conformation to naturally occurring PfAMA1.

Rabbits were immunized with FVO strain PfAMA1 or with the DiCo's either individually or as a mixture. Antibody titers and the ability to inhibit parasite growth in vitro were determined. Animals immunized with the DiCo mix performed similarly to animals immunized with FVO AMA1 when measured against FVO strain parasites, but outperformed animals immunized with FVO AMA1 when assessed against other strains. The levels of growth inhibition (70%) induced by the mix of three DiCo's were comparable for FVO, 3D7 and HB3, suggesting a considerable degree of variation in AMA1 is adequately covered.

This indicates that vaccines based upon the DiCo mix approach provide a broader functional immunity than immunisation with a single allele.

Materials and Methods

Cloning of Diversity Covering AMA-1 Sequences in *Pichia pastoris*.

Synthetic genes with optimised codon usage for *Pichia pastoris* were designed for AMA1 proteins comprising domains I, II and III of DiCo1, DiCo2 and DiCo3 (DNA2.0, San Diego). These sequences were PCR-amplified with primers X1 (5' gcg aat tca ttg aaa ttg ttg aaa gat c 3', SEQ ID No: 26) and Y1 (5' ggg gta cca aca tct tat cgt aag ttg g 3', SEQ ID No: 27), X1 and Y2 (5' ggg gta ccg aca tgt tat cgt aag ttg gc 3', SEQ ID No: 28) and X1 and Y1 for DiCo 1, 2 and 3 respectively.

The PCR products were cloned into the EcoRI-KpnI sites of the pPicZA vector (Invitrogen, Groningen) whereby the atg start codon (Met) of this vector was used for transcription initiation and used to transform *Escherichia coli* DH5 cells. After transformation of the *Escherichia coli* DH5 cells, plasmids were isolated, checked for the presence of the expected restriction sites and then used to transform *Pichia pastoris* KM71H following manufacturer's protocols.

Transformed *Pichia pastoris* colonies were tested for protein production by culture in 10 mL glycerol-containing medium a 50 ml tube for 48 hours at 29-30° C. under vigorous shaking. Cells were harvested by centrifugation (5 minutes at 2500 rpm, table top centrifuge) and resuspended in 4 ml methanol-containing medium, and then cultured for 24 hours at 29-30° C. under vigorous shaking. After low-speed centrifugation, the culture supernatant was harvested and 20 µl, was tested on SDS-gel for proteins with the expected size. The identity was confirmed by western blotting with the reduction-sensitive monoclonal antibody 4G2.

Protein Production

Fermentation runs were performed in either 3 or 7 liters fermentors (Applikon, Schiedam, The Netherlands), with initial starting volumes of 1 and 2 liters, respectively. The *Pichia pastoris* clones were grown in BMGY (1% yeast extract, 2% peptone, 1.34% yeast nitrogen base, 1% glycerol, 0.4 mg of biotin per liter, 0.1 M K-phosphate, pH 6.0) at 30° C. for 24 hours. 50 ml/liter was used to inoculate the fermentor containing minimal salt fermentation medium (per liter of medium: $MgSO_4$-$7H_2O$, 14.9 grams; $K_2SO_4$, 18.2 grams; $CaCl_2$, 0.65 grams; KOH, 4.13 grams, glycerol 40 grams, 26.7 ml 85% $H_3PO_4$ and 12 ml PTM1 trace salts solution).

During the batch phase air was sparged at 1 liter per liter initial medium volume. Temperature was kept constant throughout the fermentation at 30° C., pH was kept at 6.0, using 25% $NH_4OH$ and 85% $H_3PO_4$. Fed batch was started after the dissolved oxygen levels were back to 21%, after being down to (almost) zero, generally between 18 and 24 hours.

Subsequently, the culture was fed 50% glycerol fortified with 12 mL/liter PTM1 trace salts at a rate of 32 mL/hour per liter initial medium volume for 20 to 24 hours. During this fed-batch phase of the fermentation, the medium was sparged with 100% oxygen to keep the dissolved oxygen concentration at 21%. Lastly, the culture was induced by the addition of methanol. The first 3 hours at a rate of 1 mL/hour per liter initial medium volume, increasing to 3 mL/hour per liter initial medium volume in 3 hours, continuing at this rate for approximately 18 hours.

During the induction phase oxygen levels were maintained at 21% with 100% oxygen, but air was sparged continuously into the medium as well (at 1 liter per liter initial fermentation medium), as it was observed that keeping the oxygen level at 21% with 100% oxygen only prevented expression of some proteins.

After induction the pH of medium was increased to pH 7.8 and cooled with a cryostat to 15° C. or lower. Cells were removed by centrifugation (25 minutes, 5000×g, 4° C.) and culture medium was filtered through a 0.22 µm filter using a Quixstand hollow fibre cartridge (GE Healthcare, Etten-Leur, The Netherlands) to remove all remaining yeast cells.

The protein in the culture supernatants (2 or more Liters) were concentrated to approximately 100 mL using a Quixstand with a 10 kDa cut-off hollow fibre column, and diluted with an equal volume of demineralised water and concentrated again. This procedure was repeated four times.

Thereafter, the proteins were bound to a hydroxyapatite column (REF), equilibrated with 1 mM sodium phosphate buffer pH 8.0. The protein was eluted from the column with 50 mM sodium phosphate buffer pH 8.0. This fraction was concentrated to less than 1 ml and subsequently put on a Superdex 75 preparative size exclusion chromatography column (REF). The fractions containing the DiCo protein were pooled, concentrated and sterilized by filtration trough a 0.22 µm filter.

Rabbit Immunizations.

Rabbits were housed, immunised and blood was sampled by Eurogentec SA, Seraing, Belgium according to national animal welfare regulations. Five groups of five rabbits were immunised on days 0, 28 and 56 with *Pichia*-expressed DiCo1 (30 µg), DiCo2 (30 µg) or DiCo3 (30 µg), FVO PfAMA-1 D123 (30 µg), or a mixture of DiCo1, DiCo2 and DiCo3 (10 µg each, in total 30 µg). Montanide ISA 51 (SEPPIC, Paris, France) was used as the adjuvant. Vaccine formulations were prepared according to the manufacturers instructions (50/50 mass/mass). Antisera obtained two weeks after the third immunisation (day 70) were tested for reactivity by ELISA, and functional capacity by the in vitro Parasite Inhibition Assay.

Elisa

Enzyme-linked immunosorbent assay (ELISA) was performed in duplicate on serum samples in 96 well flat-bottomed microtitre plates (Greiner, Alphen a/d Rijn, The Netherlands), coated with 500 ng/mL purified AMA1 antigens according to published methods (Kocken 2002).

The secondary antibody was anti-rabbit IgG conjugated to alkaline phosphatase (Pierce, Rockford, Ill.). A standard curve was applied on each plate and titres of the unknowns were calculated by a four-parameter fit. Titres are expressed as arbitrary units, where 1 AU yields an OD of 1.0. Thus the amount of AU of a sample is the reciprocal dilution at which an OD of 1 will be achieved.

IgG Purification

Antibodies to be used for parasite inhibition assays were purified on protein A columns (Sigma, St Louis, Mo.) using standard protocols ENRfu(8), exchanged into RPMI 1640 using Amicon concentrators (30 kDa cutoff), filter-sterilised and stored at −20° C. until use. IgG concentrations were determined using a Nanodrop ND-1000 spectrophotometer (Nanodrop Technologies, Wilmington, Del., USA).

Parasites

*P. falciparum* strains NF54, FCR3, HB3 were cultured in vitro using standard *Plasmodium falciparum* culture techniques in an atmosphere of 5% $CO_2$, 5% $O_2$ and 90% $N_2$. FCR3 AMA-1 (accession no. M34553) differs by 1 amino acid in the pro-sequence from FVO AMA-1 (accession no. AJ277646).

In vitro Parasite Inhibition Assay (PIA)

The effect of purified IgG antibodies on parasite invasion was evaluated in triplicate using 96 well flat-bottomed plates (Greiner) with in vitro matured *Plasmodium falciparum* schizonts at a starting parasitemia of 0.2-0.4%, a haematocrit of 2.0% and a final volume of 100 µL containing 10% normal human serum, 20 µg mL$^{-1}$ gentamicin in RPMI 1640.

After 40 to 42 hours, cultures were resuspended, and 50 µL was transferred into 200 ice-cold PBS. The cultures were then centrifuged, the supernatant removed and the plates were frozen. Inhibition of parasite growth was estimated using the pLDH assay as previously described (Kennedy 2002). Parasite growth inhibition, reported as a percentage, was calculated as follows:

$$100 - ((Od_{experimental} - Od_{background})/(Od_{control} - Od_{background}) \times 100)$$

Control IgG was isolated from rabbits that had been immunised with adjuvant only.

Statistical Analysis

IgG titres were compared with Analysis of Variance (ANOVA) using log-transformed IgG titres as dependent variable and vaccine antigen as independent variable. PIA titres were analysed with linear mixed effects models, to allow for the simultaneous comparison of various IgG concentrations, whilst correcting for pseudoreplication (Paterson et al).

The PIA titre was entered as the dependent variable and log-transformed total IgG and treatment group as independent variables. Various models were fitted for each strain tested and the best fitting model was selected based on log-likelihood.

Results

Analysis of Polymorphisms in AMA-variants

All *Plasmodium falciparum* AMA1 sequences, complete sequences and fragments, available on Jan. 3, 2005 (360 in total), were retrieved from a nucleotide search in the Pubmed database (www.ncbi.nlm.nih.gov/entrez/). Duplicates were removed (U84348 [3D7], AU087598 [FVO], U33274 [3D7] and AF061332 [KF1916]) and two partial sequences for the NF7 strain were combined (U33280 and M27957). The ensuing 355 sequences were aligned with an Excel macro and polymorphic residues were identified.

To reduce the risk of incorporating data resultant from sequencing errors, polymorphic positions were defined as those that varied between sequences such that two or more of the 355 sequences carried the same amino acid substitution at that site. Using this definition, 64 of 622 amino acid positions were designated polymorphic; 9 in the prosequence (aa 1-96; 9.4%), 33 in domain 1 (aa 97-315; 15.1%), 8 in domain 2 (aa 316-425; 7.3%), 11 in domain 3 (aa 426-545; 9.2%), none in the transmembrane region (aa 546-567; 0%) and 3 in the cytoplasmic tail (aa 568-622; 5.5%). The alignment also showed that the presence of a particular amino acid at one polymorphic position was often linked to the presence of particular amino acids down—(FIG. 4) as well as upstream (FIG. 3) (i.e. in the direction of the C-terminus or N-terminus, respectively) of the protein.

Software written to identify these linkages revealed upstream linkage for 24 residues at 22 polymorphic sites. The most N-terminal member of each downstream linkage group tended not to be the predominant residue at that position (in 53 of 55 cases), although it tended to be linked to downstream residues that were the predominant (consensus) residue. Unusually, at position 197 two possible amino acids (G and D) showed downstream linkage. As exceptions in both position 172 and 283, the predominant residue linked to downstream residues and in position 200 both the predominant and minor residues are linked.

Upstream linkage was observed for 26 (27) residues at 22 polymorphic sites. The most C-terminal member of the linkage group tended not to be the predominant residue at that position and the linked upstream residues were generally the predominant (consensus) residues. Exceptionally, at position 197 all residues showed upstream linkage with position 196. The E at position 285 showed an unusual upstream linkage, in that it is linked to the non-consensus L283 and R503 is upstream linked to the non-consensus residue M496.

Design of Artificial Genes to Cover Diversity and Incorporate Linkages.

To reduce the complexity of downstream vaccine development it was felt that a maximum of three diversity-covering (DiCo) sequences could be accommodated. These DiCo's (DiCo1, DiCo2 and DiCo3), each of which comprised domains I, II and III (aa 97-545), were designed such that, when taken together, the maximal number of naturally occurring residues was incorporated, with the proviso that residues with the lowest frequencies were linked, thereby restricting the sequences. Thus over 80% of amino acids present at any given position in naturally occurring sequences and most linkages can be found back in the DiCo combination.

To restrict it to three DiCo's, 12 positions at which less than 10% of the sequences showed variation [residues: 121 (99% E), 189 (92% L), 199 (99% R), 224 (99% M), 228 (97% N), 244 (92% D), 245 (96% K), 269 (96% K), 325 (98% H), 330 (91% S), 395 (92% K) and 505 (96% F)] and four positions at which between 10 and 16% of sequences showed variation [173 (85.7% N), 175 (89.6% D), 207 (83.7% Y) and 407 (84.4% Q] were excluded. Thus, of the 52 polymorphic positions the 36 most variable were included in the design of the DiCo proteins (22/33 positions, 4/8 and 10/11 in domains I, II and III, respectively).

Three backbones were designed, taking linkages into account. DiCo1 (SEQ ID Nos: 1 and 4) was fully compliant to the down- and upstream linkages. DiCo2 (SEQ ID Nos: 2 and 5) broke downstream linkage in that H296 is linked to N448 rather than D448 as in natural AMA1 sequences and upstream linkage in that D296 is restricted by N448 whilst H296 is included. DiCo3 (SEQ ID Nos 3 and 6) incorporated the least prevalent amino acids and two restricted downstream positions were not compliant.

Normally E206 is restricted by D197/D200/L201, while DiCo3 incorporates K206. In addition, N225 is normally restricted by L201; in DiCo3 I225 is incorporated. Two upstream linkages were not compliant: H200 and F201 are restricted by K206, but D200 and L201 are included.

Non-linked polymorphisms were subsequently incorporated respectively into DiCo1, DiCo2 and DiCo3 backbones according to their frequency of occurrence. Because AMA1 is not believed to be glycosylated in malaria parasites, NxS/NxT motifs were also changed to remove potential N-glycosylation sites (SEQ ID Nos 1 to 3). Non-polymorphic residues were changed as previously described (Kocken 2002) (T288->V, S373->D, N422->D, S423->K and N499->Q). Because N162 of DiCo 1 and DiCo2 is a linked polymorphic residue as well as a potential N-glycosylation site it was changed to Q162 to avoid introducing restrictions.

FIG. 5 shows all resultant DiCo sequences (SEQ ID Nos 1 to 3) in alignment with HB3 (SEQ ID NO: 30), 3D7 (SEQ ID No: 29) and FVO (SEQ ID NO: 31) strain AMA1 and with the consensus sequence (SEQ ID NO: 25) derived from alignment of all 355 input sequences. The differences between sequences are summarised in FIG. 6, which includes a profile of differences according to AMA1 domain. DiCo1 is close to the consensus sequence (differing at only 4 positions, all of which are in Domain I); as expected DiCo2 and DiCo3 differ markedly from the consensus sequence and overall the DiCo sequences differ quite considerably from one another.

DiCo Expression in *Pichia pastoris*

Expression in small-scale fermentors resulted in protein levels of 40 mg/L or more before purification. DiCo1 was purified using Ni-IMAC chromatography. Although a hexa-His tag was also incorporated into DiCo2 and DiCo3 these did not bind to Ni-IMAC and were instead purified by sequential hydroxyapatite and size exclusion chromatography.

Figure 7:
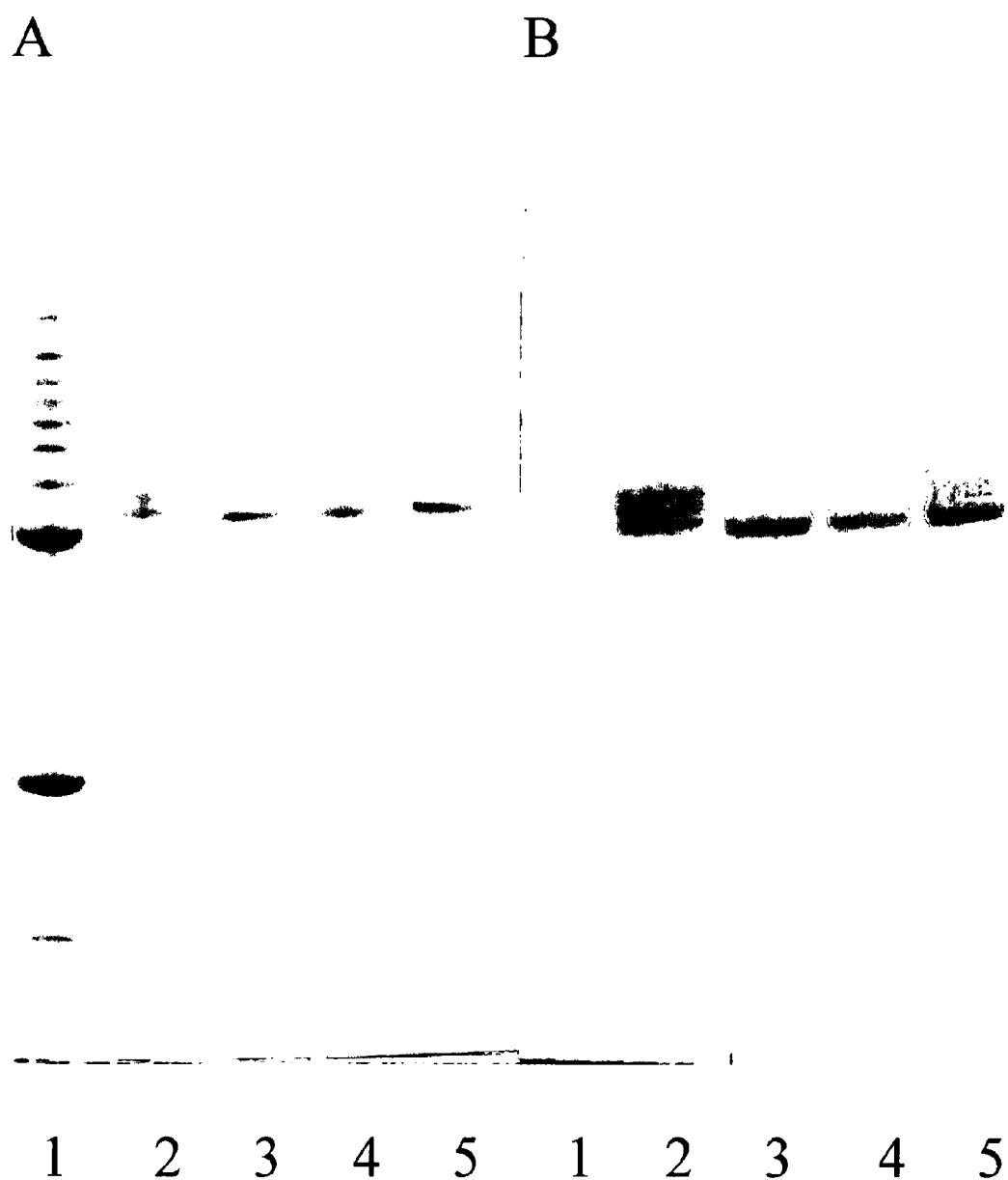
FIG. 7 panel A shows SDS-PAGE of purified DiCo's. Lane 1, Bench mark marker; lane 2, DiCo 1; lane 3, DiCo 2; lane 4. DiCo 3; lane 5, DiCo mix. Panel B shows a Western blot with 4G2 as primary antibody. Lane 1, molecular weight marker; lane 2, DiCo 1; lane 3, DiCo 2; lane 4. DiCo 3; lane 5, DiCo mix. Samples were not reduced.

Purified DiCo proteins were assessed for integrity and purity by SDS-PAGE and for antigenicity by Western blot using the reduction sensitive monoclonal antibody 4G2 (FIG. 7). The main band for all three DiCo proteins migrated with the expected size (50 kDa) and reacted with 4G2. A proportion of DiCo1 appears in a more slowly migrating band; as has been previously reported (REF) some AMA1 molecules expressed in *Pichia* may undergo O-glycosylation.

Gel analysis by a stain specific for glycosylation moieties (data not shown) suggests that this may be occurring for DiCo1, an observation that may explain the observed heterogeneity in migration.

Western blot analysis also revealed dimerisation for all three DiCo proteins, this has previously been observed with the full-length ectodomain (aa 25-545) GMP product, where it did not result in loss of potency.

Immunological and Functional Assessment

Groups of 5 rabbits were immunized three times with 30 μg of *Pichia* expressed and purified AMA1 from either FVO strain, DiCo1, DiCo2 or DiCo3 or with a mix of 10 μg of each of the three DiCo's (DiCoMix).

Figure 8:
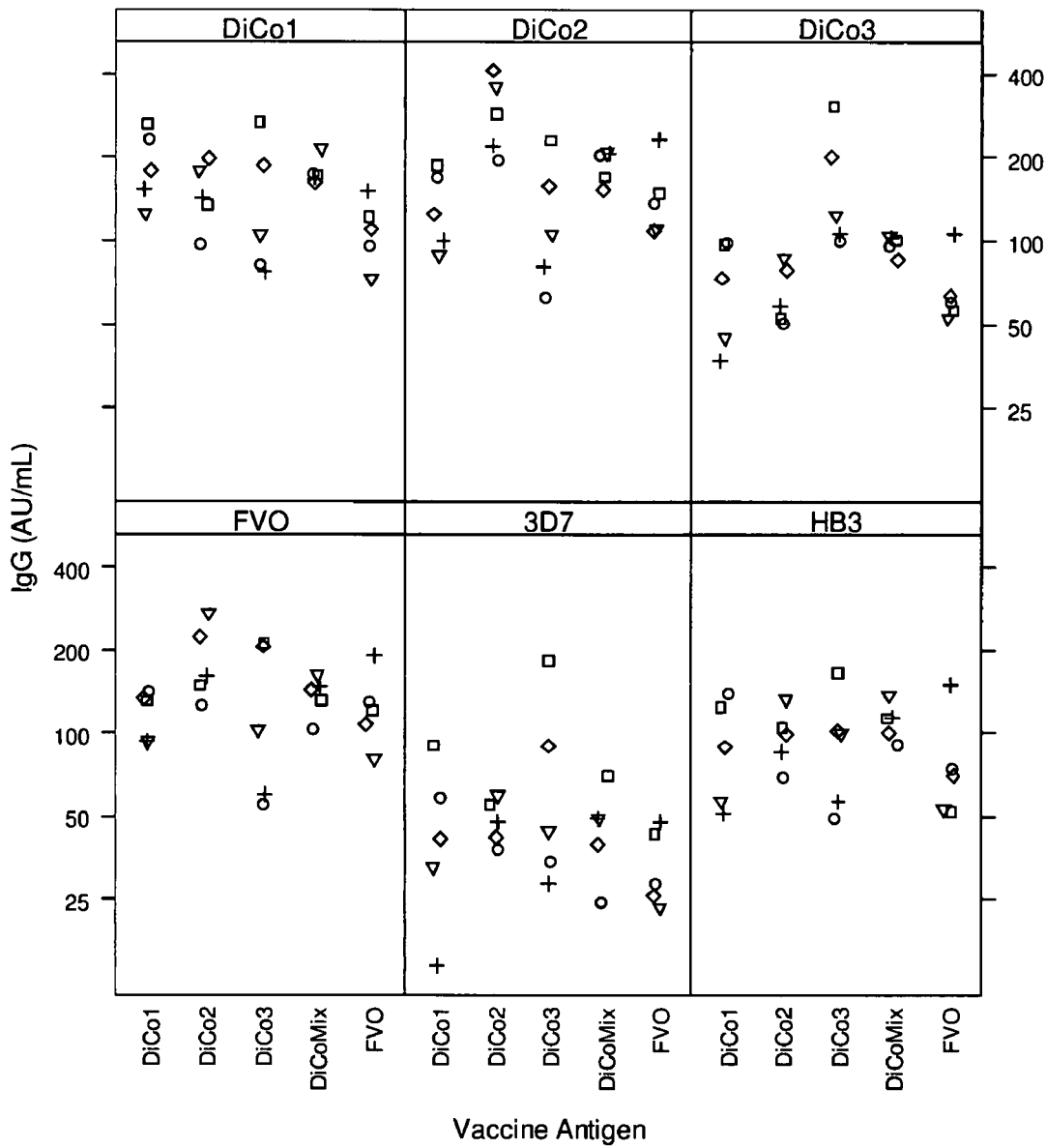
FIG. 8 shows IgG antibody levels to various AMA-1 variants. Symbols refer to single rabbits. Within each treatment group, the same symbols represent the same animals. Circles: rabbit 1, crosses: rabbit 2, triangles: rabbit 3, squares: rabbit 4 and diamonds: rabbit 5
Figure 9:
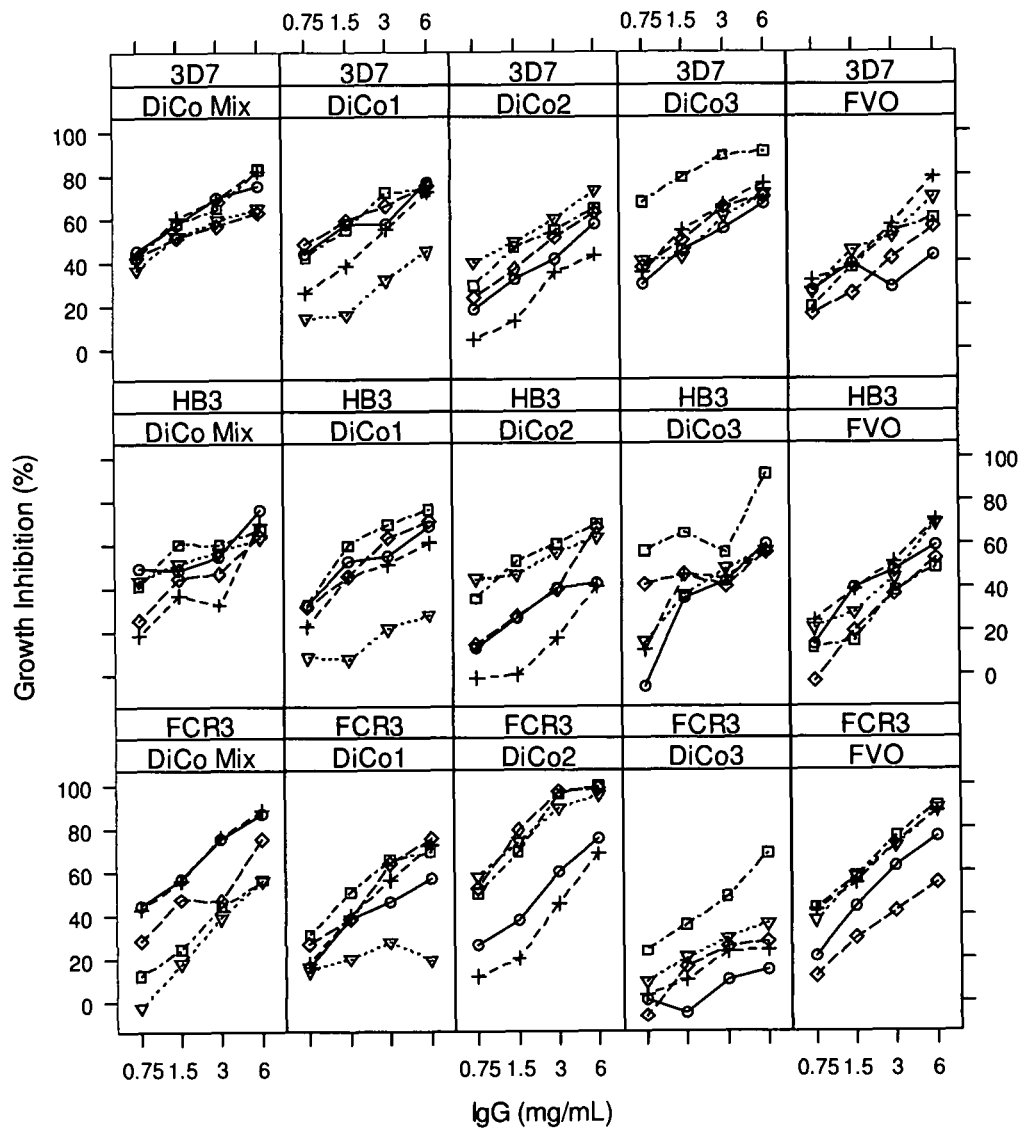
FIG. 9 shows growth inhibiting titres versus IgG. concentration on individual rabbits according to vaccine antigen and assay strain. Symbols refer to single rabbits. Within each treatment group, the same symbols represent the same animals. Circles: rabbit 1, crosses: rabbit 2, triangles: rabbit 3, squares: rabbit 4 and diamonds: rabbit 5.

Antibody levels to the immunising antigen and to AMA1 from three laboratory strains were determined by ELISA (FIGS. 8 and 9). Although none of these DiCo sequences have been observed in nature, overall they were all well recognised by antibodies from rabbits that had been immunised with FVO AMA1 and elicited antibodies that were reactive with the FVO, 3D7 and HB3 antigens, further suggestive that they attained appropriate conformation.

Rabbits immunised with DiCoMix showed responses that overall were comparable to those obtained by immunisation with single components. Moreover, for all antigens under investigation, the variation in IgG titres was smallest in the group immunised with the DiCoMix. The responses to the FVO, 3D7 and HB3 antigens did not differ significantly between the treatment groups (p=0.27, 0.48 and 0.35, respectively).

For DiCo1 there was a tendency for the FVO immunised animals to have lower titres than the DiCo1 and DiCoMix groups (p=0.09). For DiCo2, animals immunised with DiCo2 tended to have higher titres than those immunised with DiCo-Mix and DiCo1 and DiCo3 immunised animals had lower titres than animals immunised with DiCo2 (p=0.0035). The animals immunised with DiCo3 had significantly higher DiCo3 titres than the animals immunised with DiCo1, DiCo2 and DiCoMix (p=0.002).

Figure 10:
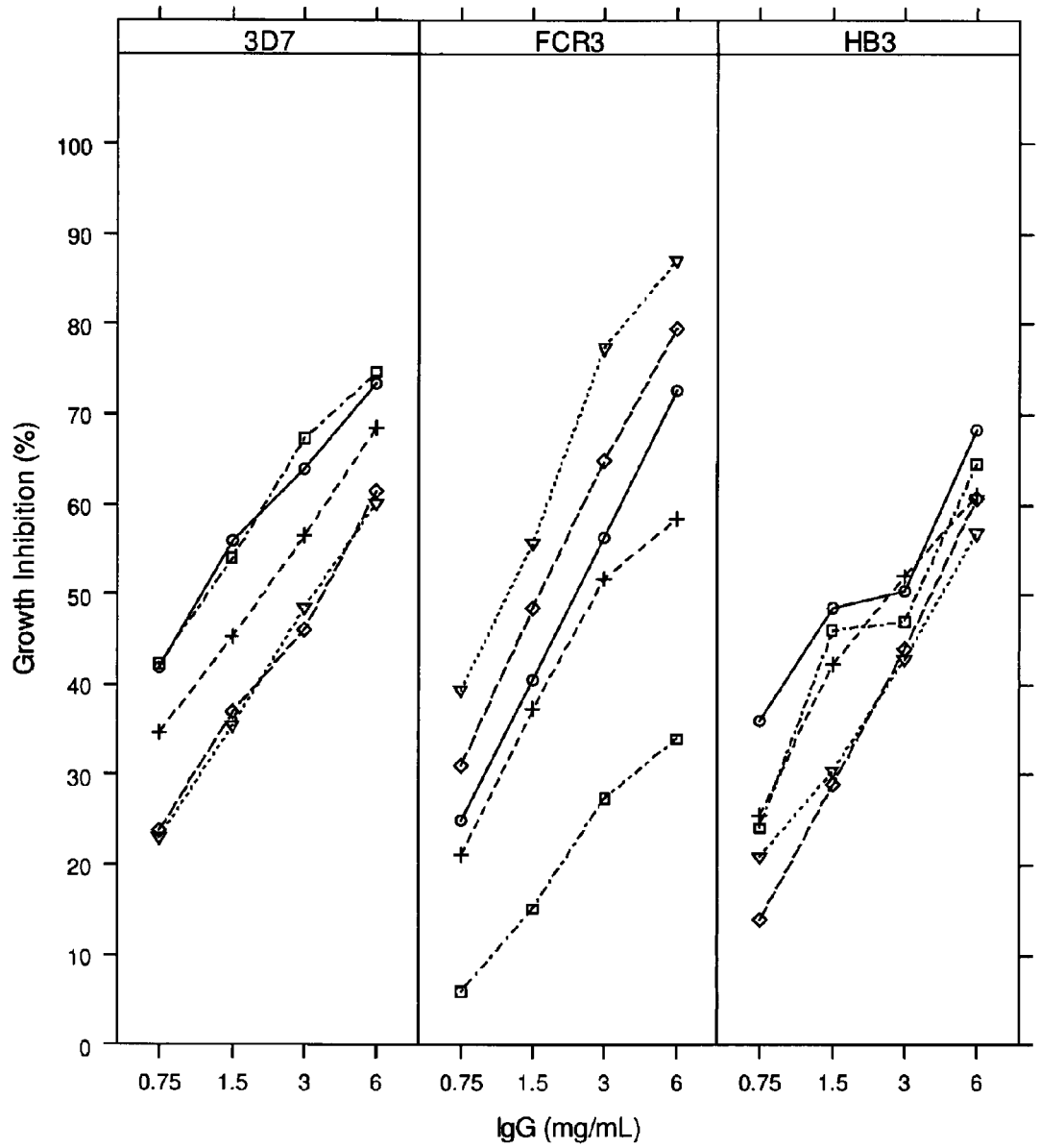
FIG. 10 shows growth inhibiting titres versus IgG concentration groups of rabbits according to vaccine antigen and assay strain. Open circles: DiCo mix, crosses: DiCo 1, triangles: DiCo 2, squares: DiCo 3 and diamonds: FVO-AMA-1.

To assess anti-parasitic effects, IgG purified from rabbit sera obtained two weeks after the final immunisation was added to synchronised asexual blood stage cultures of 3D7, FCR3 and HB3 strains (FIG. 10). The DiCoMix was always amongst the three best performing antigens with about 70% inhibition at 6 mg/mL for all three strains tested in the inhibition assay. Moreover, the DiCoMix performed nearly as well as the homologous (FVO) antigen for FCR3. All separate DiCo antigens elicited antibodies in rabbits that were active in inhibiting parasite growth. The DiCo3 antigen was not very effective for FCR-3, but it induced good functional responses to 3D7 and HB3, despite the difference of 17 or 18 amino acids for 3D7 and HB3, respectively. These observations again suggest that all antigens attained an appropriate conformation.

For the FCR3 strain the highest levels of growth inhibition were observed for the DiCo2 group, followed by FVO, DiCo-Mix, DiCo1 and DiCo3, respectively. For each doubling in total IgG levels, inhibition levels increased by 16% (95% CI: 13% to 19%) for all groups except DiCo3, where the increase of inhibition per IgG doubling was significantly lower [−6.3 (95% CI: −10.5 to −2.0)]. The level of inhibition in the DiCo-Mix group at 1 mg/mL IgG was estimated at 31% (95% CI: 18 to 45%). There was a tendency for an increased level of inhibition at 1 mg/mL for the DiCo2 group (16% higher 95% CI: −4 to 35%), whereas the level of inhibition at 1 mg/mL IgG was significantly lower in the DiCo3 group (−21%, 95% CI −41 to −2).

For the HB3 strain the highest levels of growth inhibition were observed for the DiCoMix group, followed by DiCo3, DiCo1, FVO and DiCo2, respectively. Growth inhibition levels increased by 12% (95% CI: 11 to 14) for each doubling of total IgG. There were no significant between group differences for the effect of IgG on inhibition. The level of inhibition at 1 mg/mL total IgG was estimated at 38% (95% CI: 27 to 49%). There was a tendency for the DiCo2 and FVO groups to have lower levels of inhibition at 1 mg/mL [−13 (95% CI: −29 to 3] and −14 (95% CI: −30 to 2), respectively].

For the 3D7 strain the highest levels of inhibition were observed for the DiCo3 and DiCoMix groups, followed by DiCo1, FVO and DiCo2, respectively. Inhibition levels increased by 11% (95% CI: 10 to 12) for each doubling in total IgG. There were no significant between group differences for the effect of IgG on inhibition. The level of inhibition at 1 mg/mL total IgG was estimated at 46% (95% CI: 37 to 55%). Both DiCo 2 and FVO had significantly lower levels of inhibition at 1 mg/mL total IgG [−17 (95% C −30 to −4) and −17 (95% CI 30 to −3), respectively).

Discussion

The development of an effective *Plasmodium falciparum* AMA1-based vaccine is difficult because of the polymorphic nature of the vaccine candidate and the immune selection pressure exerted upon it. An effective vaccine is expected to induce responses to conserved determinants as well as to the broadest range of allele-specific determinants. Failure to cover a sufficient amount of the allele-specific determinants found in AMA1 will, most likely, favor the breakthrough of variants and thereby compromise vaccine efficacy.

The AMA1-based vaccines currently in development are based on one or two naturally occurring allelic forms of AMA1 (BPRC, NIH, WRAIR, Pan CPII) and may therefore not cover an amount of variation sufficient to prevent the escape of certain allelic forms.

Coverage can be improved by simply extending the number of alleles included, but cost constraints dictate that only a limited number of alleles can be included. This becomes even more important when several different vaccine candidates are to be combined, as the total numbers and amounts of protein to be included in a malaria vaccine are limited too.

An alternative way to improve coverage is through the use of a limited number of artificial variants designed to optimally cover polymorphisms. From the data presented here we can conclude that diversity covering sequences can be produced, including a sequence that is very close to the consensus. The proteins all react with a conformation-sensitive monoclonal antibody. Moreover, sera elicited by the DiCo sequences all react with naturally occurring alleles and these sequences elicit antibodies that inhibit parasite growth. Indicative that each single DiCo protein is conformationally correct.

The DiCo approach could be considered somewhat naïve, as many epitopes within AMA1 are conformational and may also be discontinuous (crystal structure papers, Thomas refs). However, by incorporating most of the linked residues, stretches of naturally occurring amino acids are present in each single DiCo and therefore a number of conformational epitopes are likely to be preserved. This is corroborated by the observation that all individual DiCo sequences induce growth-inhibiting antibodies to the three laboratory strains tested.

The data presented show that a combination of 3 artificial alleles induces levels of growth inhibiting antibodies to the three strains investigated that are comparable to the levels induced by a homologous antigen (e.g. FVO antigen on FCR3), indicating that a considerable amount diversity is covered by the combination.

Moreover, the DiCo3 antigen yielded high levels (±70%) of growth inhibiting antibody to the 3D7 and HB3 strains, despite being 17 and 18 amino acids different from the 3D7 and HB3 antigens, respectively.

A further aspect of the DiCo proteins is that they can be combined into fusion proteins thereby further reducing the amount of components in a malaria vaccine. This fusion protein can then be further extended by the inclusion of other, preferably small, vaccine candidates. One such candidate is the $MSP1_{19}$, for which a fusion protein with AMA1 has been produced.

It is possible to make 3 DiCo's that completely incorporate linkage patterns. However, the strategy used here was to assign the residues according to observed prevalence, with the most prevalent going into DiCo1 and the least prevalent into DiCo3. This has led to a number of linkage breaks in DiCo's 2 and 3.

---

The invention claimed is:

1. An isolated protein composition comprising three artificial AMA1 antigens comprising SEQ ID Nos 1-3.

2. The isolated protein composition according to claim 1, wherein said AM1 antigen is a protein of a *Plasmodium* species selected from the group consisting of *falciparum, vivax, knowlesi, malariae* and *ovale*.

3. The isolated protein composition according to claim 2, wherein the AMA1 antigens comprise variable amino acid positions selected from the group consisting of 162, 167, 172, 173, 175, 187, 190, 196, 197, 200, 201, 204, 206, 207, 225, 230, 242, 243, 267, 282, 283, 285, 296, 300, 308, 332, 393, 404, 405, 407, 435, 439, 448, 451, 485, 493, 496, 503, 512 and 544 of said AMA1 protein of *Plasmodium falciparum*.

4. The isolated protein composition according to claim 1, further comprising at least one additional artificial AMA1 antigen comprising an amino acid sequence chosen from SEQ ID Nos 4 to 12.

5. The isolated protein composition according to claim 1, further comprising at least one additional artificial AMA1 antigen comprising an amino acid sequence chosen from SEQ ID Nos 4-6.

6. The isolated protein composition according to claim 1, wherein said antigens are linked.

7. An isolated protein variant comprising an amino acid sequence selected from the group consisting of SEQ ID Nos 1 to 12.

8. The isolated protein variant according to claim 7, wherein said amino acid sequence is selected from the group consisting of SEQ ID Nos 1 to 6.

9. The isolated protein variant according to claim 7, wherein said amino acid sequence is selected from the group consisting of SEQ ID Nos 1 to 3.

10. An isolated protein composition comprising three artificial AMA1 antigens comprising SEQ ID Nos 4-6.

11. The isolated protein composition according to claim 10, wherein the AMA1 antigens comprise variable amino acid positions selected from the group consisting of 162, 167, 172, 173, 175, 187, 190, 196, 197, 200, 201, 204, 206, 207, 225, 230, 242, 243, 267, 282, 283, 285, 296, 300, 308, 332, 393, 404, 405, 407, 435, 439, 448, 451, 485, 493, 496, 503, 512 and 544 of said AMA1 protein of *Plasmodium falciparum*.

12. The isolated protein composition according to claim 10, further comprising at least one additional artificial AMA1 antigen comprising an amino acid sequence chosen from SEQ ID Nos 1-3 and 7-12.

* * * * *

UNITED STATES PATENT AND TRADEMARK OFFICE
CERTIFICATE OF CORRECTION

PATENT NO. : 8,741,305 B2  
APPLICATION NO. : 12/520344  
DATED : June 3, 2014  
INVENTOR(S) : Alan William Thomas Page 1 of 1

It is certified that error appears in the above-identified patent and that said Letters Patent is hereby corrected as shown below:

Title Page, item (75) Inventors, Line 1, delete "Bishop (NL);" and insert -- Boskoop (NL); --

In the Claims

Column 71, Line 26, Claim 2, delete "AM1" and insert -- AMA1 --

Signed and Sealed this  
Ninth Day of September, 2014

Michelle K. Lee  
*Deputy Director of the United States Patent and Trademark Office*

SEQUENCE LISTING

```
<160> NUMBER OF SEQ ID NOS: 31

<210> SEQ ID NO 1
<211> LENGTH: 449
<212> TYPE: PRT
<213> ORGANISM: Artificial
<220> FEATURE:
<223> OTHER INFORMATION: Diversity covering (DiCo) protein variant 1
      without glycosylation sites

<400> SEQUENCE: 1

Ile Glu Ile Val Glu Arg Ser Asn Tyr Met Gly Asn Pro Trp Thr Glu
1               5                   10                  15

Tyr Met Ala Lys Tyr Asp Ile Glu Val His Gly Ser Gly Ile Arg
            20                  25                  30

Val Asp Leu Gly Glu Asp Ala Glu Val Ala Gly Thr Gln Tyr Arg Leu
            35                  40                  45

Pro Ser Gly Lys Cys Pro Val Phe Gly Lys Gly Ile Ile Ile Glu Asn
        50                  55                  60

Ser Gln Thr Thr Phe Leu Thr Pro Val Ala Thr Glu Asn Gln Asp Leu
65                  70                  75                  80

Lys Asp Gly Gly Phe Ala Phe Pro Pro Thr Lys Pro Leu Met Ser Pro
                85                  90                  95

Met Thr Leu Asp Gln Met Arg His Phe Tyr Lys Asp Asn Glu Tyr Val
            100                 105                 110

Lys Asn Leu Asp Glu Leu Thr Leu Cys Ser Arg His Ala Gly Asn Met
        115                 120                 125

Asn Pro Asp Asn Asp Lys Asn Ser Asn Tyr Lys Tyr Pro Ala Val Tyr
    130                 135                 140

Asp Asp Lys Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Ser Phe Gln Asn Tyr Val
            180                 185                 190

Tyr Leu Ser Lys Asn Val Val Asp Asn Trp Glu Lys Val Cys Pro Arg
        195                 200                 205

Lys Asn Leu Glu Asn Ala Lys Phe Gly Leu Trp Val Asp Gly Asn Cys
    210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270
```

```
Asn Lys Asn Ala Asp Met Ile Lys Ser Ala Phe Leu Pro Thr Gly Ala
        275                 280                 285

Phe Lys Ala Asp Arg Tyr Lys Ser His Gly Lys Gly Tyr Asn Trp Gly
        290                 295                 300

Asn Tyr Asn Arg Lys Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                    325                 330                 335

His Pro Ile Glu Val Glu His Asn Phe Pro Cys Ser Leu Tyr Lys Asp
                340                 345                 350

Glu Ile Lys Lys Glu Ile Glu Arg Glu Ser Lys Arg Ile Lys Leu Asn
                355                 360                 365

Asp Asn Asp Asp Glu Gly Asn Lys Lys Ile Ile Ala Pro Arg Ile Phe
        370                 375                 380

Ile Ser Asp Asp Lys Asp Ser Leu Lys Cys Pro Cys Asp Pro Glu Ile
385                 390                 395                 400

Val Ser Gln Ser Thr Cys Asn Phe Phe Val Cys Lys Cys Val Glu Lys
                    405                 410                 415

Arg Ala Glu Val Thr Ser Asn Asn Glu Val Val Val Lys Glu Glu Tyr
                420                 425                 430

Lys Asp Glu Tyr Ala Asp Ile Pro Glu His Lys Pro Thr Tyr Asp Lys
        435                 440                 445

Met

<210> SEQ ID NO 2
<211> LENGTH: 449
<212> TYPE: PRT
<213> ORGANISM: Artificial
<220> FEATURE:
<223> OTHER INFORMATION: Diversity covering (DiCo) protein variant 2
      without glycosylation sites

<400> SEQUENCE: 2

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
                20                  25                  30

Val Asp Leu Gly Glu Asp Ala Val Ala Gly Thr Gln Tyr Arg Leu
            35                  40                  45

Pro Ser Gly Lys Cys Pro Val Phe Gly Lys Gly Ile Ile Ile Glu Asn
    50                  55                  60

Ser Gln Thr Thr Phe Leu Lys Pro Val Ala Thr Gly Asn Gln Asp Leu
65                  70                  75                  80

Lys Asp Gly Gly Phe Ala Phe Pro Pro Thr Asn Pro Leu Ile Ser Pro
                85                  90                  95

Met Thr Leu Asn Gly Met Arg Asp Phe Tyr Lys Asn Asn Glu Tyr Val
                100                 105                 110

Lys Asn Leu Asp Glu Leu Thr Leu Cys Ser Arg His Ala Gly Asn Met
        115                 120                 125

Asn Pro Asp Asn Asp Glu Asn Ser Asn Tyr Lys Tyr Pro Ala Val Tyr
        130                 135                 140

Asp Tyr Asn Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Leu Phe Glu Asn Tyr Val
```

```
                180                 185                 190
Tyr Leu Ser Lys Asn Val Val His Asn Trp Glu Glu Val Cys Pro Arg
            195                 200                 205
Lys Asn Leu Glu Asn Ala Lys Phe Gly Leu Trp Val Asp Gly Asn Cys
            210                 215                 220
Glu Asp Ile Pro His Val Asn Glu Phe Ser Ala Asn Asp Leu Phe Glu
225                 230                 235                 240
Cys Asn Lys Leu Val Phe Glu Leu Ser Ala Ser Asp Gln Pro Lys Gln
            245                 250                 255
Tyr Glu Gln His Leu Thr Asp Tyr Glu Lys Ile Lys Glu Gly Phe Lys
            260                 265                 270
Asn Lys Asn Ala Asp Met Ile Lys Ser Ala Phe Leu Pro Thr Gly Ala
            275                 280                 285
Phe Lys Ala Asp Arg Tyr Lys Ser Arg Gly Lys Gly Tyr Asn Trp Gly
            290                 295                 300
Asn Tyr Asn Arg Lys Thr Gln Lys Cys Glu Ile Phe Asn Val Lys Pro
305                 310                 315                 320
Thr Cys Leu Ile Asn Asp Lys Ser Tyr Ile Ala Thr Thr Ala Leu Ser
            325                 330                 335
His Pro Ile Glu Val Glu Asn Asn Phe Pro Cys Ser Leu Tyr Lys Asn
            340                 345                 350
Glu Ile Met Lys Glu Ile Glu Arg Glu Ser Lys Arg Ile Lys Leu Asn
            355                 360                 365
Asp Asn Asp Asp Glu Gly Asn Lys Lys Ile Ile Ala Pro Arg Ile Phe
370                 375                 380
Ile Ser Asp Asp Lys Ser Leu Lys Cys Pro Cys Asp Pro Glu Met
385                 390                 395                 400
Val Ser Gln Ser Thr Cys Arg Phe Phe Val Cys Lys Cys Val Glu Arg
            405                 410                 415
Arg Ala Glu Val Thr Ser Asn Asn Glu Val Val Lys Glu Glu Tyr
            420                 425                 430
Lys Asp Glu Tyr Ala Asp Ile Pro Glu His Lys Pro Thr Tyr Asp Asn
            435                 440                 445
Met

<210> SEQ ID NO 3
<211> LENGTH: 449
<212> TYPE: PRT
<213> ORGANISM: Artificial
<220> FEATURE:
<223> OTHER INFORMATION: Diversity covering (DiCo) protein variant 3
      without glycosylation sites

<400> SEQUENCE: 3

Ile Glu Ile Val Glu Arg Ser Asn Tyr Met Gly Asn Pro Trp Thr Glu
1               5                   10                  15
Tyr Met Ala Lys Tyr Asp

Met Thr Leu Asp Asp Met Arg Asp Leu Tyr Lys Asp Asn Lys Tyr Val
              100                 105                 110

Lys Asn Leu Asp Glu Leu Thr Leu Cys Ser Arg His Ala Gly Asn Met
            115                 120                 125

Ile Pro Asp Asn Asp Lys Asn Ser Asn Tyr Lys Tyr Pro Ala Val Tyr
        130                 135                 140

Asp Tyr Glu Asp Lys Lys Cys His Ile Leu Tyr Ile Ala Ala Gln Glu
145                 150                 155                 160

Asn Asn Gly Pro Arg Tyr Cys Asn Lys Asp Gln Ser Lys Arg Asn Ser
                165                 170                 175

Met Phe Cys Phe Arg Pro Ala Lys Asp Ile Ser Phe Gln Asn Tyr Val
            180                 185                 190

Tyr Leu Ser Lys Asn Val Val Asp Asn Trp Glu Lys Val Cys Pro Arg
        195                 200                 205

Lys Asn Leu Gln Asn Ala Lys Phe Gly Leu Trp Val Asp Gly Asn Cys
        210                 215                 220

Glu Asp Ile Pro His Val Asn Glu Phe Ser Ala Ile Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Lys Ile Lys Glu Gly Phe Lys
            260                 265                 270

Asn Lys Asn Ala Asp Met Ile Lys Ser Ala Phe Leu Pro Thr Gly Ala
        275                 280                 285

Phe Lys Ala Asp Arg Tyr Lys Ser His Gly Lys Gly Tyr Asn Trp Gly
    290                 295                 300

Asn Tyr Asn Thr Glu Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                325                 330                 335

His Pro Asn Glu Val Glu His Asn Phe Pro Cys Ser Leu Tyr Lys Asp
            340                 345                 350

Glu Ile Lys Lys Glu Ile Glu Arg Glu Ser Lys Arg Ile Lys Leu Asn
        355                 360                 365

Asp Asn Asp Asp Glu Gly Asn Lys Lys Ile Ile Ala Pro Arg Ile Phe
        370                 375                 380

Ile Ser Asp Asp Ile Asp Ser Leu Lys Cys Pro Cys Ala Pro Glu Ile
385                 390                 395                 400

Val Ser Gln Ser Thr Cys Asn Phe Phe Val Cys Lys Cys Val Glu Lys
                405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Lys
        435                 440                 445

Met

<210> SEQ ID NO 4
<211> LENGTH: 449
<212> TYPE: PRT
<213> ORGANISM: Artificial
<220> FEATURE:
<223> OTHER INFORMATION: Diversity covering (DiCo) protein variant 1

<400> SEQUENCE: 4

Ile Glu Ile Val Glu Arg Ser Asn Tyr Met Gly Asn Pro Trp Thr Glu

-continued

```
1               5                   10                  15
Tyr Met Ala Lys Tyr Asp Ile Glu Glu Val His Gly Ser Gly Ile Arg
                20                  25                  30

Val Asp Leu Gly Glu Asp Ala Glu Val Ala Gly Thr Gln Tyr Arg Leu
                35                  40                  45

Pro Ser Gly Lys Cys Pro Val Phe Gly Lys Gly Ile Ile Ile Glu Asn
                50                  55                  60

Ser Asn Thr Thr Phe Leu Thr Pro Val Ala Thr Glu Asn Gln Asp Leu
65                          70                  75                  80

Lys Asp Gly Gly Phe Ala Phe Pro Pro Thr Lys Pro Leu Met Ser Pro
                        85                  90                  95

Met Thr Leu Asp Gln Met Arg His Phe Tyr Lys Asp Asn Glu Tyr Val
                100                 105                 110

Lys Asn Leu Asp Glu Leu Thr Leu Cys Ser Arg His Ala Gly Asn Met
                115                 120                 125

Asn Pro Asp Asn Asp Lys Asn Ser Asn Tyr Lys Tyr Pro Ala Val Tyr
                130                 135                 140

Asp Asp Lys Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Ser Phe Gln Asn Tyr Thr
                180                 185                 190

Tyr Leu Ser Lys Asn Val Val Asp Asn Trp Glu Lys Val Cys Pro Arg
                195                 200                 205

Lys Asn Leu Glu Asn Ala Lys Phe Gly Leu Trp Val Asp Gly Asn Cys
                210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
                260                 265                 270

Asn Lys Asn Ala Ser Met Ile Lys Ser Ala Phe Leu Pro Thr Gly Ala
                275                 280                 285

Phe Lys Ala Asp Arg Tyr Lys Ser His Gly Lys Gly Tyr Asn Trp Gly
                290                 295                 300

Asn Tyr Asn Arg Lys Thr Gln Lys Cys Glu Ile Phe Asn Val Lys Pro
305                 310                 315                 320

Thr Cys Leu Ile Asn Asn Ser Ser Tyr Ile Ala Thr Ala Leu Ser
                325                 330                 335

His Pro Ile Glu Val Glu His Asn Phe Pro Cys Ser Leu Tyr Lys Asp
                340                 345                 350

Glu Ile Lys Lys Glu Ile Glu Arg Glu Ser Lys Arg Ile Lys Leu Asn
                355                 360                 365

Asp Asn Asp Asp Glu Gly Asn Lys Lys Ile Ile Ala Pro Arg Ile Phe
                370                 375                 380

Ile Ser Asp Asp Lys Asp Ser Leu Lys Cys Pro Cys Asp Pro Glu Ile
385                 390                 395                 400

Val Ser Asn Ser Thr Cys Asn Phe Phe Val Cys Lys Cys Val Glu Lys
                        405                 410                 415

Arg Ala Glu Val Thr Ser Asn Asn Glu Val Val Lys Glu Glu Tyr
                420                 425                 430
```

```
Lys Asp Glu Tyr Ala Asp Ile Pro Glu His Lys Pro Thr Tyr Asp Lys
            435                 440                 445
Met
```

<210> SEQ ID NO 5
<211> LENGTH: 449
<212> TYPE: PRT
<213> ORGANISM: Artificial
<220> FEATURE:
<223> OTHER INFORMATION: Diversity covering (DiCo) protein variant 2

<400> SEQUENCE: 5

```
Ile Glu Ile Val Glu Arg Ser Asn Tyr Met Gly Asn Pro Trp Thr Glu
1               5                   10                  15

Tyr Met Ala Lys Tyr Asp Ile Glu Val His Gly Ser Gly Ile Arg
            20                  25                  30

Val Asp Leu Gly Glu Asp Ala Glu Val Ala Gly Thr Gln Tyr Arg Leu
            35                  40                  45

Pro Ser Gly Lys Cys Pro Val Phe Gly Lys Gly Ile Ile Ile Glu Asn
            50                  55                  60

Ser Asn Thr Thr Phe Leu Lys Pro Val Ala Thr Gly Asn Gln Asp Leu
65                  70                  75                  80

Lys Asp Gly Gly Phe Ala Phe Pro Pro Thr Asn Pro Leu Ile Ser Pro
            85                  90                  95

Met Thr Leu Asn Gly Met Arg Asp Phe Tyr Lys Asn Asn Glu Tyr Val
            100                 105                 110

Lys Asn Leu Asp Glu Leu Thr Leu Cys Ser Arg His Ala Gly Asn Met
            115                 120                 125

Asn Pro Asp Asn Asp Glu Asn Ser Asn Tyr Lys Tyr Pro Ala Val Tyr
            130                 135                 140

Asp Tyr Asn Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
            165                 170                 175

Met Phe Cys Phe Arg Pro Ala Lys Asp Lys Leu Phe Glu Asn Tyr Thr
            180                 185                 190

Tyr Leu Ser Lys Asn Val Val His Asn Trp Glu Glu Val Cys Pro Arg
            195                 200                 205

Lys Asn Leu Glu Asn Ala Lys Phe Gly Leu Trp Val Asp Gly Asn Cys
            210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
            245                 250                 255

Tyr Glu Gln His Leu Thr Asp Tyr Glu Lys Ile Lys Glu Gly Phe Lys
            260                 265                 270

Asn Lys Asn Ala Ser Met Ile Lys Ser Ala Phe Leu Pro Thr Gly Ala
            275                 280                 285

Phe Lys Ala Asp Arg Tyr Lys Ser Arg Gly Lys Gly Tyr Asn Trp Gly
            290                 295                 300

Asn Tyr Asn Arg Lys Thr Gln Lys Cys Glu Ile Phe Asn Val Lys Pro
305                 310                 315                 320

Thr Cys Leu Ile Asn Asn Ser Ser Tyr Ile Ala Thr Thr Ala Leu Ser
            325                 330                 335

His Pro Ile Glu Val Glu Asn Asn Phe Pro Cys Ser Leu Tyr Lys Asn
            340                 345                 350
```

```
Glu Ile Met Lys Glu Ile Glu Arg Glu Ser Lys Arg Ile Lys Leu Asn
            355                 360                 365

Asp Asn Asp Asp Glu Gly Asn Lys Lys Ile Ile Ala Pro Arg Ile Phe
        370                 375                 380

Ile Ser Asp Asp Lys Asp Ser Leu Lys Cys Pro Cys Asp Pro Glu Met
385                 390                 395                 400

Val Ser Asn Ser Thr Cys Arg Phe Phe Val Cys Lys Cys Val Glu Arg
                405                 410                 415

Arg Ala Glu Val Thr Ser Asn Asn Glu Val Val Val Lys Glu Glu Tyr
            420                 425                 430

Lys Asp Glu Tyr Ala Asp Ile Pro Glu His Lys Pro Thr Tyr Asp Asn
            435                 440                 445

Met

<210> SEQ ID NO 6
<211> LENGTH: 449
<212> TYPE: PRT
<213> ORGANISM: Artificial
<220> FEATURE:
<223> OTHER INFORMATION: Diversity covering (DiCo) protein variant 3

<400> SEQUENCE: 6

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Lys Thr Thr Phe Leu Thr Pro Val Ala Thr Glu Asn Gln Asp Leu
65                  70                  75                  80

Lys Asp Gly Gly Phe Ala Phe Pro Pro Thr Glu Pro Leu Met Ser Pro
                85                  90                  95

Met Thr Leu Asp Asp Met Arg Asp Leu Tyr Lys Asp Asn Lys Tyr Val
            100                 105                 110

Lys Asn Leu Asp Glu Leu Thr Leu Cys Ser Arg His Ala Gly Asn Met
        115                 120                 125

Ile Pro Asp Asn Asp Lys Asn Ser Asn Tyr Lys Tyr Pro Ala Val Tyr
    130                 135                 140

Asp Tyr Glu Asp Lys Lys Cys His Ile Leu Tyr Ile Ala Ala Gln Glu
145                 150                 155                 160

Asn Asn Gly Pro Arg Tyr Cys Asn Lys Asp Gln Ser Lys Arg Asn Ser
                165                 170                 175

Met Phe Cys Phe Arg Pro Ala Lys Asp Ile Ser Phe Gln Asn Tyr Thr
            180                 185                 190

Tyr Leu Ser Lys Asn Val Val Asp Asn Trp Glu Lys Val Cys Pro Arg
        195                 200                 205

Lys Asn Leu Gln Asn Ala Lys Phe Gly Leu Trp Val Asp Gly Asn Cys
    210                 215                 220

Glu Asp Ile Pro His Val Asn Glu Phe Ser Ala Ile Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
```

```
                      260                 265                 270
Asn Lys Asn Ala Ser Met Ile Lys Ser Ala Phe Leu Pro Thr Gly Ala
            275                 280                 285
Phe Lys Ala Asp Arg Tyr Lys Ser His Gly Lys Gly Tyr Asn Trp Gly
            290                 295                 300
Asn Tyr Asn Thr Glu Thr Gln Lys Cys Glu Ile Phe Asn Val Lys Pro
305                 310                 315                 320
Thr Cys Leu Ile Asn Asn Ser Ser Tyr Ile Ala Thr Ala Leu Ser
            325                 330                 335
His Pro Asn Glu Val Glu His Asn Phe Pro Cys Ser Leu Tyr Lys Asp
            340                 345                 350
Glu Ile Lys Lys Glu Ile Glu Arg Glu Ser Lys Arg Ile Lys Leu Asn
            355                 360                 365
Asp Asn Asp Asp Glu Gly Asn Lys Lys Ile Ile Ala Pro Arg Ile Phe
            370                 375                 380
Ile Ser Asp Asp Ile Asp Ser Leu Lys Cys Pro Cys Ala Pro Glu Ile
385                 390                 395                 400
Val Ser Asn Ser Thr Cys Asn Phe Phe Val Cys Lys Cys Val Glu Lys
            405                 410                 415
Arg Ala Glu Val Thr Ser Asn Asn Glu Val Val Lys Glu Glu Tyr
            420                 425                 430
Lys Asp Glu Tyr Ala Asp Ile Pro Glu His Lys Pro Thr Tyr Asp Lys
            435                 440                 445
Met

<210> SEQ ID NO 7
<211> LENGTH: 449
<212> TYPE: PRT
<213> ORGANISM: Artificial
<220> FEATURE:
<223> OTHER INFORMATION: Diversity covering (DiCo) protein variant 4
      without glycosylation sites

<400> SEQUENCE: 7

Ile Glu Ile Val Glu Arg Ser Asn Tyr Met Gly Asn Pro Trp Thr Glu
1               5                   10                  15
Tyr Met Ala Lys Tyr Asp Ile Glu Glu Val His Gly Ser Gly Ile Arg
            20                  25                  30
Val Asp Leu Gly Glu Asp Ala Glu Val Ala Gly Th

```
Met Phe Cys Phe Arg Pro Ala Lys Asp Lys Ser Phe Gln Asn Tyr Val
            180                 185                 190
Tyr Leu Ser Lys Asn Val Val Asp Asn Trp Glu Lys Val Cys Pro Arg
            195                 200                 205
Lys Asn Leu Glu Asn Ala Lys Phe Gly Leu Trp Val Asp Gly Asn Cys
210                 215                 220
Glu Asp Ile Pro His Val Asn Glu Phe Ser Ala Ile Asp Leu Phe Glu
225                 230                 235                 240
Cys Asn Lys Leu Val Phe Glu Leu Ser Ala Ser Asp Gln Pro Lys Gln
            245                 250                 255
Tyr Glu Gln His Leu Thr Asp Tyr Glu Lys Ile Lys Glu Gly Phe Lys
            260                 265                 270
Asn Lys Asn Ala Asp Met Ile Lys Ser Ala Phe Leu Pro Thr Gly Ala
            275                 280                 285
Phe Lys Ala Asp Arg Tyr Lys Ser His Gly Lys Gly Tyr Asn Trp Gly
            290                 295                 300
Asn Tyr Asn Arg Lys Thr Gln Lys Cys Glu Ile Phe Asn Val Lys Pro
305                 310                 315                 320
Thr Cys Leu Ile Asn Asp Lys Ser Tyr Ile Ala Thr Thr Ala Leu Ser
            325                 330                 335
His Pro Ile Glu Val Glu His Asn Phe Pro Cys Ser Leu Tyr Lys Asp
            340                 345                 350
Glu Ile Lys Lys Glu Ile Glu Arg Glu Ser Lys Arg Ile Lys Leu Asn
            355                 360                 365
Asp Asn Asp Asp Glu Gly Asn Lys Lys Ile Ile Ala Pro Arg Ile Phe
            370                 375                 380
Ile Ser Asp Asp Lys Asp Ser Leu Lys Cys Pro Cys Asp Pro Glu Ile
385                 390                 395                 400
Val Ser Gln Ser Thr Cys Asn Phe Phe Val Cys Lys Cys Val Glu Lys
            405                 410                 415
Arg Ala Glu Val Thr Ser Asn Asn Glu Val Val Val Lys Glu Glu Tyr
            420                 425                 430
Lys Asp Glu Tyr Ala Asp Ile Pro Glu His Lys Pro Thr Tyr Asp Lys
            435                 440                 445
Met

<210> SEQ ID NO 8
<211> LENGTH: 449
<212> TYPE: PRT
<213> ORGANISM: Artificial
<220> FEATURE:
<223> OTHER INFORMATION: Diversity covering (DiCo) protein variant 5
      without glycosylation sites

<400> SEQUENCE: 8

Ile Glu Ile Val Glu Arg Ser Asn Tyr Met Gly Asn Pro Trp Thr Glu
1               5                   10                  15
Tyr Met Ala Lys Tyr Asp Ile Glu Glu Val His Gly Ser Gly Ile Arg
            20                  25                  30
Val Asp Leu Gly Glu Asp Ala Glu Val Ala Gly Thr Gln Tyr Arg Leu
        35                  40                  45
Pro Ser Gly Lys Cys Pro Val Phe Gly Lys Gly Ile Ile Ile Glu Asn
    50                  55                  60
Ser Lys Thr Thr Phe Leu Thr Pro Val Ala Thr Glu Asn Gln Asp Leu
65                  70                  75                  80
```

```
Lys Asp Gly Gly Phe Ala Phe Pro Pro Thr Glu Pro Leu Ile Ser Pro
                85                  90                  95

Met Thr Leu Asn Gly Met Arg Asp Phe Tyr Lys Asn Asn Glu Tyr Val
            100                 105                 110

Lys Asn Leu Asp Glu Leu Thr Leu Cys Ser Arg His Ala Gly Asn Met
            115                 120                 125

Asn Pro Asp Asn Asp Glu Asn Ser Asn Tyr Lys Tyr Pro Ala Val Tyr
            130                 135                 140

Asp Tyr Asn Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Leu Phe Glu Asn Tyr Val
            180                 185                 190

Tyr Leu Ser Lys Asn Val Val Asp Asn Trp Glu Lys Val Cys Pro Arg
            195                 200                 205

Lys Asn Leu Glu Asn Ala Lys Phe Gly Leu Trp Val Asp Gly Asn Cys
            210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Asp Met Ile Lys Ser Ala Phe Leu Pro Thr Gly Ala
            275                 280                 285

Phe Lys Ala Asp Arg Tyr Lys Ser His Gly Lys Gly Tyr Asn Trp Gly
290                 295                 300

Asn Tyr Asn Arg Lys Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                325                 330                 335

His Pro Ile Glu Val Glu His Asn Phe Pro Cys Ser Leu Tyr Lys Asn
            340                 345                 350

Glu Ile Met Lys Glu Ile Glu Arg Glu Ser Lys Arg Ile Lys Leu Asn
            355                 360                 365

Asp Asn Asp Asp Glu Gly Asn Lys Lys Ile Ile Ala Pro Arg Ile Phe
            370                 375                 380

Ile Ser Asp Asp Lys Asp Ser Leu Lys Cys Pro Cys Asp Pro Glu Ile
385                 390                 395                 400

Val Ser Gln Ser Thr Cys Asn Phe Phe Val Cys Lys Cys Val Glu Lys
                405                 410                 415

Arg Ala Glu Val Thr Ser Asn Asn Glu Val Val Val Lys Glu Glu Tyr
            420                 425                 430

Lys Asp Glu Tyr Ala Asp Ile Pro Glu His Lys Pro Thr Tyr Asp Lys
            435                 440                 445

Met

<210> SEQ ID NO 9
<211> LENGTH: 449
<212> TYPE: PRT
<213> ORGANISM: Artificial
<220> FEATURE:
<223> OTHER INFORMATION: Diversity covering (DiCo) protein variant 6
      without glycosylation sites
```

<400> SEQUENCE: 9

```
Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Gln Thr Thr Phe Leu Lys Pro Val Ala Thr Gly Asn Gln Asp Leu
65                  70                  75                  80

Lys Asp Gly Gly Phe Ala Phe Pro Pro Thr Asn Pro Leu Met Ser Pro
                85                  90                  95

Met Thr Leu Asp Asp Met Arg Asp Leu Tyr Lys Asp Asn Glu Tyr Val
            100                 105                 110

Lys Asn Leu Asp Glu Leu Thr Leu Cys Ser Arg His Ala Gly Asn Met
        115                 120                 125

Asn Pro Asp Asn Asp Lys Asn Ser Asn Tyr Lys Tyr Pro Ala Val Tyr
    130                 135                 140

Asp Asp Lys Asp Lys Lys Cys His Ile Leu Tyr Ile Ala Ala Gln Glu
145                 150                 155                 160

Asn Asn Gly Pro Arg Tyr Cys Asn Lys Asp Gln Ser Lys Arg Asn Ser
                165                 170                 175

Met Phe Cys Phe Arg Pro Ala Lys Asp Ile Ser Phe Gln Asn Tyr Val
            180                 185                 190

Tyr Leu Ser Lys Asn Val Val His Asn Trp Glu Glu Val Cys Pro Arg
        195                 200                 205

Lys Asn Leu Gln Asn Ala Lys Phe Gly Leu Trp Val Asp Gly Asn Cys
    210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Asp Met Ile Lys Ser Ala Phe Leu Pro Thr Gly Ala
        275                 280                 285

Phe Lys Ala Asp Arg Tyr Lys Ser Arg Gly Lys Gly Tyr Asn Trp Gly
    290                 295                 300

Asn Tyr Asn Thr Glu Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                325                 330                 335

His Pro Asn Glu Val Glu Asn Asn Phe Pro Cys Ser Leu Tyr Lys Asp
            340                 345                 350

Glu Ile Lys Lys Glu Ile Glu Arg Glu Ser Lys Arg Ile Lys Leu Asn
        355                 360                 365

Asp Asn Asp Asp Glu Gly Asn Lys Lys Ile Ile Ala Pro Arg Ile Phe
    370                 375                 380

Ile Ser Asp Asp Ile Asp Ser Leu Lys Cys Pro Cys Ala Pro Glu Met
385                 390                 395                 400

Val Ser Gln Ser Thr Cys Arg Phe Phe Val Cys Lys Cys Val Glu Arg
                405                 410                 415
```

Arg Ala Glu Val Thr Ser Asn Asn Glu Val Val Lys Glu Glu Tyr
          420                 425                 430

Lys Asp Glu Tyr Ala Asp Ile Pro Glu His Lys Pro Thr Tyr Asp Asn
          435                 440                 445

Met

<210> SEQ ID NO 10
<211> LENGTH: 449
<212> TYPE: PRT
<213> ORGANISM: Artificial
<220> FEATURE:
<223> OTHER INFORMATION: Diversity covering (DiCo) protein variant 4

<400> SEQUENCE: 10

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Asn Thr Thr Phe Leu Thr Pro Val Ala Thr Glu Asn Gln Asp Leu
65                  70                  75                  80

Lys Asp Gly Gly Phe Ala Phe Pro Pro Thr Lys Pro Leu Met Ser Pro
                85                  90                  95

Met Thr Leu Asp Gln Met Arg His Phe Tyr Lys Asp Asn Lys Tyr Val
            100                 105                 110

Lys Asn Leu Asp Glu Leu Thr Leu Cys Ser Arg His Ala Gly Asn Met
        115                 120                 125

Ile Pro Asp Asn Asp Lys Asn Ser Asn Tyr Lys Tyr Pro Ala Val Tyr
    130                 135                 140

Asp Tyr Glu Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Ser Phe Gln Asn Tyr Thr
            180                 185                 190

Tyr Leu Ser Lys Asn Val Val Asp Asn Trp Glu Lys Val Cys Pro Arg
        195                 200                 205

Lys Asn Leu Glu Asn Ala Lys Phe Gly Leu Trp Val Asp Gly Asn Cys
    210                 215                 220

Glu Asp Ile Pro His Val Asn Glu Phe Ser Ala Ile Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Ser Met Ile Lys Ser Ala Phe Leu Pro Thr Gly Ala
        275                 280                 285

Phe Lys Ala Asp Arg Tyr Lys Ser His Gly Lys Gly Tyr Asn Trp Gly
    290                 295                 300

Asn Tyr Asn Arg Lys Thr Gln Lys Cys Glu Ile Phe Asn Val Lys Pro
305                 310                 315                 320

Thr Cys Leu Ile Asn Asn Ser Ser Tyr Ile Ala Thr Thr Ala Leu Ser
                325                 330                 335

```
His Pro Ile Glu Val Glu His Asn Phe Pro Cys Ser Leu Tyr Lys Asp
            340                 345                 350
Glu Ile Lys Lys Glu Ile Glu Arg Glu Ser Lys Arg Ile Lys Leu Asn
            355                 360             365
Asp Asn Asp Asp Glu Gly Asn Lys Lys Ile Ile Ala Pro Arg Ile Phe
            370                 375                 380
Ile Ser Asp Asp Lys Asp Ser Leu Lys Cys Pro Cys Asp Pro Glu Ile
385             390                 395                 400
Val Ser Asn Ser Thr Cys Asn Phe Phe Val Cys Lys Cys Val Glu Lys
                405                 410             415
Arg Ala Glu Val Thr Ser Asn Asn Glu Val Val Lys Glu Glu Tyr
                420             425                 430
Lys Asp Glu Tyr Ala Asp Ile Pro Glu His Lys Pro Thr Tyr Asp Lys
            435                 440                 445
Met

<210> SEQ ID NO 11
<211> LENGTH: 449
<212> TYPE: PRT
<213> ORGANISM: Artificial
<220> FEATURE:
<223> OTHER INFORMATION: Diversity covering (DiCo) protein variant 5

<400> SEQUENCE: 11

Ile Glu Ile Val Glu Arg Ser Asn Tyr Met Gly Asn Pro Trp Thr Glu
1               5                   10                  15
Tyr Met Ala Lys Tyr Asp Ile Glu Glu Val His Gly Ser Gly Ile Arg
            20                  25                  30
Val Asp Leu Gly Glu Asp Ala Glu Val Ala Gly Thr Gln Tyr Arg Leu
            35                  40                  45
Pro Ser Gly

```
                    245                 250                 255
Tyr Glu Gln His Leu Thr Asp Tyr Glu Lys Ile Lys Glu Gly Phe Lys
            260                 265                 270

Asn Lys Asn Ala Ser Met Ile Lys Ser Ala Phe Leu Pro Thr Gly Ala
        275                 280                 285

Phe Lys Ala Asp Arg Tyr Lys Ser His Gly Lys Gly Tyr Asn Trp Gly
        290                 295                 300

Asn Tyr Asn Arg Lys Thr Gln Lys Cys Glu Ile Phe Asn Val Lys Pro
305                 310                 315                 320

Thr Cys Leu Ile Asn Asn Ser Ser Tyr Ile Ala Thr Thr Ala Leu Ser
                325                 330                 335

His Pro Ile Glu Val Glu His Asn Phe Pro Cys Ser Leu Tyr Lys Asn
                340                 345                 350

Glu Ile Met Lys Glu Ile Glu Arg Glu Ser Lys Arg Ile Lys Leu Asn
                355                 360                 365

Asp Asn Asp Asp Glu Gly Asn Lys Lys Ile Ile Ala Pro Arg Ile Phe
        370                 375                 380

Ile Ser Asp Asp Lys Asp Ser Leu Lys Cys Pro Cys Asp Pro Glu Ile
385                 390                 395                 400

Val Ser Asn Ser Thr Cys Asn Phe Phe Val Cys Lys Cys Val Glu Lys
                405                 410                 415

Arg Ala Glu Val Thr Ser Asn Asn Glu Val Val Lys Glu Glu Tyr
                420                 425                 430

Lys Asp Glu Tyr Ala Asp Ile Pro Glu His Lys Pro Thr Tyr Asp Lys
        435                 440                 445

Met

<210> SEQ ID NO 12
<211> LENGTH: 449
<212> TYPE: PRT
<213> ORGANISM: Artificial
<220> FEATURE:
<223> OTHER INFORMATION: Diversity covering (DiCo) protein variant 6

<400> SEQUENCE: 12

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
        50                  55                  60

Ser Asn Thr Thr Phe Leu Lys Pro Val Ala Thr Gly Asn Gln Asp Leu
65                  70                  75                  80

Lys Asp Gly Gly Phe Ala Phe Pro Pro Thr Asn Pro Leu Met Ser Pro
            85                  90                  95

Met Thr Leu Asp Asp Met Arg Asp Leu Tyr Lys Asp Asn Glu Tyr Val
        100                 105                 110

Lys Asn Leu Asp Glu Leu Thr Leu Cys Ser Arg His Ala Gly Asn Met
        115                 120                 125

Asn Pro Asp Asn Asp Lys Asn Ser Asn Tyr Lys Tyr Pro Ala Val Tyr
        130                 135                 140

Asp Asp Lys Asp Lys Lys Cys His Ile Leu Tyr Ile Ala Ala Gln Glu
145                 150                 155                 160
```

```
Asn Asn Gly Pro Arg Tyr Cys Asn Lys Asp Gln Ser Lys Arg Asn Ser
            165                 170                 175

Met Phe Cys Phe Arg Pro Ala Lys Asp Ile Ser Phe Gln Asn Tyr Thr
            180                 185                 190

Tyr Leu Ser Lys Asn Val Val His Asn Trp Glu Glu Val Cys Pro Arg
            195                 200                 205

Lys Asn Leu Gln Asn Ala Lys Phe Gly Leu Trp Val Asp Gly Asn Cys
            210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
            245                 250                 255

Tyr Glu Gln His Leu Thr Asp Tyr Glu Lys Ile Lys Glu Gly Phe Lys
            260                 265                 270

Asn Lys Asn Ala Ser Met Ile Lys Ser Ala Phe Leu Pro Thr Gly Ala
            275                 280                 285

Phe Lys Ala Asp Arg Tyr Lys Ser Arg Gly Lys Gly Tyr Asn Trp Gly
            290                 295                 300

Asn Tyr Asn Thr Glu Thr Gln Lys Cys Glu Ile Phe Asn Val Lys Pro
305                 310                 315                 320

Thr Cys Leu Ile Asn Asn Ser Ser Tyr Ile Ala Thr Thr Ala Leu Ser
            325                 330                 335

His Pro Asn Glu Val Glu Asn Phe Pro Cys Ser Leu Tyr Lys Asp
            340                 345                 350

Glu Ile Lys Lys Glu Ile Glu Arg Glu Ser Lys Arg Ile Lys Leu Asn
            355                 360                 365

Asp Asn Asp Asp Glu Gly Asn Lys Lys Ile Ile Ala Pro Arg Ile Phe
370                 375                 380

Ile Ser Asp Asp Ile Asp Ser Leu Lys Cys Pro Cys Ala Pro Glu Met
385                 390                 395                 400

Val Ser Asn Ser Thr Cys Arg Phe Phe Val Lys Cys Val Glu Arg
            405                 410                 415

Arg Ala Glu Val Thr Ser Asn Asn Glu Val Val Val Lys Glu Glu Tyr
            420                 425                 430

Lys Asp Glu Tyr Ala Asp Ile Pro Glu His Lys Pro Thr Tyr Asp Asn
            435                 440                 445

Met

<210> SEQ ID NO 13
<211> LENGTH: 1353
<212> TYPE: DNA
<213> ORGANISM: Artificial
<220> FEATURE:
<223> OTHER INFORMATION: nucleic acid sequence encoding SEQ ID NO: 1

<400> SEQUENCE: 13
atgattgaaa ttgttgaaag atctaactac atgggtaacc catggactga atacatggct      60
aagtacgata ttgaagaagt tcatggttct ggtattagag ttgatttggg tgaagatgct     120
gaagttgctg gtactcaata cagattgcca tctggtaagt gtccagtttt tggtaagggt     180
attattattg aaaactctca aactactttt ttgactccag ttgctactga aaaccaagat     240
ttgaaggatg gtggttttgc ttttccacca actaagccat tgatgtctcc aatgactttg     300
gatcaaatga cattttta caaggataac gaatacgtta agaacttgga tgaattgact     360
ttgtgttcta gacatgctgg taacatgaac ccagataacg ataagaactc taactacaag     420
```

```
tacccagctg tttacgatga taaggataag aagtgtcata ttttgtacat tgctgctcaa    480
gaaaacaacg gtccaagata ctgtaacaag gatgaatcta agagaaactc tatgttttgt    540
tttagaccag ctaaggataa gtcttttcaa aactacgttt acttgtctaa gaacgttgtt    600
gataactggg aaaaggtttg tccaagaaag aacttggaaa acgctaagtt tggtttgtgg    660
gttgatggta actgtgaaga tattccacat gttaacgaat tttctgctaa cgatttgttt    720
gaatgtaaca agttggtttt tgaattgtct gcttctgatc aaccaaagca atacgaacaa    780
catttgactg attacgaaaa gattaaggaa ggttttaaga acaagaacgc tgatatgatt    840
aagtctgctt ttttgccaac tggtgctttt aaggctgata gatacaagtc tcatggtaag    900
ggttacaact ggggtaacta acacagaaag actcaaaagt gtgaaatttt taacgttaag    960
ccaacttgtt tgattaacga taagtcttac attgctacta ctgctttgtc tcatccaatt   1020
gaagttgaac ataactttcc atgttctttg tacaaggatg aaattaagaa ggaaattgaa   1080
agagaatcta agagaattaa gttgaacgat aacgatgatg aaggtaacaa gaagattatt   1140
gctccaagaa ttttttatttc tgatgataag gattctttga agtgtccatg tgatccagaa   1200
attgtttctc aatctacttg taactttttt gtttgtaagt gtgttgaaaa gagagctgaa   1260
gttacttcta acaacgaagt tgttgttaag gaagaataca aggatgaata cgctgatatt   1320
ccagaacata agccaactta cgataagatg taa                                 1353
```

<210> SEQ ID NO 14
<211> LENGTH: 1350
<212> TYPE: DNA
<213> ORGANISM: Artificial
<220> FEATURE:
<223> OTHER INFORMATION: nucleic acid sequence encoding SEQ ID NO: 2

<400> SEQUENCE: 14

```
attgaaattg ttgaaagatc taactacatg ggtaacccat ggactgaata catggctaag     60
tacgatattg aagaagttca tggttctggt attagagttg atttgggtga agatgctgaa    120
gttgctggta ctcaatacag attgccatct ggtaagtgtc cagtttttgg taagggtatt    180
attattgaaa actctcaaac tactttttg aagccagttg ctactggtaa ccaagatttg     240
aaggatggtg ttttgctttt tccaccaact aacccattga tttctccaat gactttgaac    300
ggtatgagag atttttacaa gaacaacgaa tacgttaaga acttggatga attgactttg    360
tgttctagac atgctggtaa catgaaccca gataacgatg aaaactctaa ctacaagtac    420
ccagctgttt acgattacaa cgataagaag tgtcatattt tgtacattgc tgctcaagaa    480
aacaacggtc caagatactg taacaaggat gaatctaaga gaaactctat gttttgtttt    540
agaccagcta aggataagtt gtttgaaaac tacgtttact tgtctaagaa cgttgttcat    600
aactgggaag aagtttgtcc aagaaagaac ttggaaaacg ctaagtttgg tttgtgggtt    660
gatggtaact gtgaagatat tccacatgtt aacgaattttt ctgctaacga tttgtttgaa    720
tgtaacaagt tggtttttga attgtctgct tctgatcaac aaagcaata cgaacaacat    780 ttgactgatt acgaaaagat taaggaaggt tttaagaaca agaacgctga tatgattaag    840 tctgctttttt tgccaactgg tgcttttaag gctgatagat acaagtctag aggtaagggt    900
tacaactggg gtaactacaa cagaaagact caaaagtgtg aaatttttaa cgttaagcca    960
acttgtttga ttaacgataa gtcttacatt gctactactg ctttgtctca tccaattgaa   1020
gttgaaaaca acttttccatg ttcttttgtac aagaacgaaa ttatgaagga aattgaaaga   1080
gaatctaaga gaattaagtt gaacgataac gatgatgaag gtaacaagaa gattattgct   1140
```

```
ccaagaattt ttatttctga tgataaggat tctttgaagt gtccatgtga tccagaaatg   1200
gtttctcaat ctacttgtag attttttgtt tgtaagtgtg ttgaaagaag agctgaagtt   1260
acttctaaca acgaagttgt tgttaaggaa gaatacaagg atgaatacgc tgatattcca   1320
gaacataagc caacttacga taacatgtaa                                    1350
```

<210> SEQ ID NO 15
<211> LENGTH: 1350
<212> TYPE: DNA
<213> ORGANISM: Artificial
<220> FEATURE:
<223> OTHER INFORMATION: nucleic acid sequence encoding SEQ ID NO: 3

<400> SEQUENCE: 15

```
attgaaattg ttgaaagatc taactacatg ggtaacccat ggactgaata catggctaag     60
tacgatattg aagaagttca tggttctggt attagagttg atttgggtga agatgctgaa    120
gttgctggta ctcaatacag attgccatct ggtaagtgtc cagttttttgg taagggtatt   180 attattgaaa actctaagac tacttttttg actccagttg ctactgaaaa ccaagatttg    240
aaggatggtg ttttttgcttt tccaccaact gaaccattga tgtctccaat gactttggat    300
gatatgagag atttgtacaa ggataacaag tacgttaaga acttggatga attgactttg    360
tgttctagac atgctggtaa catgattcca gataacgata gaactctaa ctacaagtac     420 ccagctgttt acgattacga agataagaag tgtcatattt tgtacattgc tgctcaagaa    480
aacaacggtc aagatactg taacaaggat caatctaaga gaaactctat gttttgtttt    540
agaccagcta aggatatttc ttttcaaaac tacgtttact tgtctaagaa cgttgttgat    600
aactgggaaa aggtttgtcc aagaaagaac ttgcaaaacg ctaagtttgg tttgtgggtt    660
gatggtaact gtgaagatat tccacatgtt aacgaatttt ctgctattga tttgtttgaa    720
tgtaacaagt tgttttttga attgtctgct tctgatcaac aaagcaata cgaacaacat     780 ttgactgatt acgaaaagat taaggaaggt tttaagaaca gaacgctga tatgattaag     840 tctgcttttt tgccaactgg tgcttttaag gctgatagat acaagtctca tggtaagggt    900
tacaactggg gtaactacaa cactgaaact caaaagtgtg aaattttaa cgttaagcca    960 acttgtttga ttaacgataa gtcttacatt gctactactg ctttgtctca tccaaacgaa   1020
gttgaacata cttttccatg ttctttgtac aaggatgaaa ttaagaagga aattgaaaga   1080
gaatctaaga gaattaagtt gaacgataac gatgatgaag gtaacaagaa gattattgct   1140
ccaagaattt ttatttctga tgatattgat tctttgaagt gtccatgtgc tccagaaatt   1200
gtttctcaat ctacttgtaa cttttttgtt tgtaagtgtg ttgaaagag agctgaagtt    1260 acttctaaca acgaagttgt tgttaaggaa gaatacaagg atgaatacgc tgatattcca   1320
gaacataagc caacttacga taagatgtaa                                    1350
```

<210> SEQ ID NO 16
<211> LENGTH: 1350
<212> TYPE: DNA
<213> ORGANISM: Artificial
<220> FEATURE:
<223> OTHER INFORMATION: nucleic acid sequence encoding SEQ ID NO: 4

<400> SEQUENCE: 16

```
attgaaattg ttgaaagatc taactacatg ggtaacccat ggactgaata catggctaag     60
tacgatattg aagaagttca tggttctggt attagagttg atttgggtga agatgctgaa    120
gttgctggta ctcaatacag attgccatct ggtaagtgtc cagttttttgg taagggtatt   180
```

```
attattgaaa actctaacac tacttttttg actccagttg ctactgaaaa ccaagatttg    240
aaggatggtg gttttgcttt tccaccaact aagccattga tgtctccaat gactttggat    300
caaatgagac attttttacaa ggataacgaa tacgttaaga acttggatga attgactttg    360
tgttctagac atgctggtaa catgaaccca gataacgata agaactctaa ctacaagtac    420
ccagctgttt acgatgataa ggataagaag tgtcatattt tgtacattgc tgctcaagaa    480
aacaacggtc caagatactg taacaaggat gaatctaaga gaaactctat gttttgtttt    540
agaccagcta aggataagtc ttttcaaaac tacacttact tgtctaagaa cgttgttgat    600
aactgggaaa aggtttgtcc aagaaagaac ttggaaaacg ctaagtttgg tttgtgggtt    660
gatggtaact gtgaagatat tccacatgtt aacgaatttt ctgctaacga tttgtttgaa    720
tgtaacaagt tggtttttga attgtctgct tctgatcaac caaagcaata cgaacaacat    780
ttgactgatt acgaaaagat taaggaaggt tttaagaaca agaacgcttc tatgattaag    840
tctgcttttt tgccaactgg tgcttttaag gctgatagat acaagtctca tggtaagggt    900
tacaactggg gtaactacaa cagaaagact caaaagtgtg aaatttttaa cgttaagcca    960
acttgtttga ttaacaactc ttcttacatt gctactactg ctttgtctca tccaattgaa    1020
gttgaacata actttccatg ttctttgtac aaggatgaaa ttaagaagga aattgaaaga    1080
gaatctaaga gaattaagtt gaacgataac gatgatgaag gtaacaagaa gattattgct    1140
ccaagaattt ttatttctga tgataaggat tctttgaagt gtccatgtga tccagaaatt    1200
gtttctaact ctacttgtaa cttttttgtt tgtaagtgtg ttgaaaagag agctgaagtt    1260
acttctaaca acgaagttgt tgttaaggaa gaatacaagg atgaatacgc tgatattcca    1320
gaacataagc caacttacga taagatgtaa                                     1350
```

<210> SEQ ID NO 17
<211> LENGTH: 1350
<212> TYPE: DNA
<213> ORGANISM: Artificial
<220> FEATURE:
<223> OTHER INFORMATION: nucleic acid sequence encoding SEQ ID NO: 5

<400> SEQUENCE: 17

```
attgaaattg ttgaaagatc taactacatg ggtaacccat ggactgaata catggctaag    60
tacgatattg aagaagttca tggttctggt attagagttg atttgggtga agatgctgaa    120
gttgctggta ctcaatacag attgccatct ggtaagtgtc cagttttgg taagggtatt    180 attattgaaa actctaacac tacttttttg aagccagttg ctactggtaa ccaagatttg    240
aaggatggtg gttttgcttt tccaccaact aacccattga tttctccaat gactttgaac    300
ggtatgagag attttttacaa gaacaacgaa tacgttaaga acttggatga attgactttg    360
tgttctagac atgctggtaa catgaaccca gataacgatg aaaactctaa ctacaagtac    420
ccagctgttt acgattacaa cgataagaag tgtcatattt tgtacattgc tgctcaagaa    480
aacaacggtc caagatactg taacaaggat gaatctaaga gaaactctat gttttgtttt    540
agaccagcta aggataagtt gtttgaaaac tacacttact tgtctaagaa cgttgttcat    600
aactgggaag aagtttgtcc aagaaagaac ttggaaaacg ctaagtttgg tttgtgggtt    660
gatggtaact gtgaagatat tccacatgtt aacgaatttt ctgctaacga tttgtttgaa    720
tgtaacaagt tggtttttga attgtctgct tctgatcaac caaagcaata cgaacaacat    780
ttgactgatt acgaaaagat taaggaaggt tttaagaaca agaacgcttc tatgattaag    840
tctgcttttt tgccaactgg tgcttttaag gctgatagat acaagtctag aggtaagggt    900
```

| | |
|---|---|
| tacaactggg gtaactacaa cagaaagact caaaagtgtg aaattttttaa cgttaagcca | 960 |
| acttgtttga ttaacaactc ttcttacatt gctactactg ctttgtctca tccaattgaa | 1020 |
| gttgaaaaca actttccatg ttctttgtac aagaacgaaa ttatgaagga aattgaaaga | 1080 |
| gaatctaaga gaattaagtt gaacgataac gatgatgaag gtaacaagaa gattattgct | 1140 |
| ccaagaattt ttatttctga tgataaggat tctttgaagt gtccatgtga tccagaaatg | 1200 |
| gtttctaact ctacttgtag atttttttgtt tgtaagtgtg ttgaaagaag agctgaagtt | 1260 |
| acttctaaca acgaagttgt tgttaaggaa gaatacaagg atgaatacgc tgatattcca | 1320 |
| gaacataagc caacttacga taacatgtaa | 1350 |

<210> SEQ ID NO 18
<211> LENGTH: 1350
<212> TYPE: DNA
<213> ORGANISM: Artificial
<220> FEATURE:
<223> OTHER INFORMATION: nucleic acid sequence encoding SEQ ID NO: 6

<400> SEQUENCE: 18

| | |
|---|---|
| attgaaattg ttgaaagatc taactacatg ggtaacccat ggactgaata catggctaag | 60 |
| tacgatattg aagaagttca tggttctggt attagagttg atttgggtga agatgctgaa | 120 |
| gttgctggta ctcaatacag attgccatct ggtaagtgtc cagttttttgg taagggtatt | 180 |
| attattgaaa actctaagac tacttttttg actccagttg ctactgaaaa ccaagatttg | 240 |
| aaggatggtg gttttgcttt tccaccaact gaaccattga tgtctccaat gactttggat | 300 |
| gatatgagag atttgtacaa ggataacaag tacgttaaga acttggatga attgactttg | 360 |
| tgttctagac atgctggtaa catgattcca gataacgata gaactctaaa ctacaagtac | 420 |
| ccagctgttt acgattacga agataagaag tgtcatattt tgtacattgc tgctcaagaa | 480 |
| aacaacggtc caagatactg taacaaggat caatctaaga gaaactctat gttttgtttt | 540 |
| agaccagcta aggatatttc ttttcaaaac tacacttact tgtctaagaa cgttgttgat | 600 |
| aactgggaaa aggtttgtcc aagaaagaac ttgcaaaacg ctaagtttgg tttgtgggtt | 660 |
| gatggtaact gtgaagatat tccacatgtt aacgaatttt ctgctattga tttgtttgaa | 720 |
| tgtaacaagt tggttttttga attgtctgct tctgatcaac caagcaata cgaacaacat | 780 |
| ttgactgatt acgaaaagat taaggaaggt tttaagaaca gaacgcttc tatgattaag | 840 |
| tctgcttttt tgccaactgg tgcttttaag gctgatagat acaagtctca tggtaagggt | 900 |
| tacaactggg gtaactacaa cactgaaact caaaagtgtg aaattttttaa cgttaagcca | 960 |
| acttgtttga ttaacaactc ttcttacatt gctactactg ctttgtctca tccaaacgaa | 1020 |
| gttgaacata actttccatg ttctttgtac aaggatgaaa ttaagaagga aattgaaaga | 1080 |
| gaatctaaga gaattaagtt gaacgataac gatgatgaag gtaacaagaa gattattgct | 1140 |
| ccaagaattt ttatttctga tgatattgat tctttgaagt gtccatgtgc tccagaaatt | 1200 |
| gtttctaact ctacttgtaa ctttttttgtt tgtaagtgtg ttgaaagaga agctgaagtt | 1260 |
| acttctaaca acgaagttgt tgttaaggaa gaatacaagg atgaatacgc tgatattcca | 1320 |
| gaacataagc caacttacga taagatgtaa | 1350 |

<210> SEQ ID NO 19
<211> LENGTH: 1350
<212> TYPE: DNA
<213> ORGANISM: Artificial
<220> FEATURE:
<223> OTHER INFORMATION: nucleic acid sequence encoding SEQ ID NO: 7

<400> SEQUENCE: 19

```
attgaaattg ttgaaagatc taactacatg ggtaacccat ggactgaata catggctaag    60
tacgatattg aagaagttca tggttctggt attagagttg atttgggtga agatgctgaa   120
gttgctggta ctcaatacag attgccatct ggtaagtgtc cagttttttgg taagggtatt  180
attattgaaa actctcaaac tacttttttg actccagttg ctactgaaaa ccaagatttg   240
aaggatggtg gttttgcttt tccaccaact aagccattga tgtctccaat gactttggat   300
caaatgagac attttacaa ggataacaag tacgttaaga acttggatga attgactttg    360
tgttctagac atgctggtaa catgattcca gataacgata gaactctaa ctacaagtac    420
ccagctgttt acgattacga agataagaag tgtcatattt tgtacattgc tgctcaagaa   480
aacaacggtc aagatactg taacaaggat gaatctaaga gaaactctat gttttgtttt    540
agaccagcta aggataagtc cttttcaaaac tacgtttact tgtctaagaa cgttgttgat  600
aactgggaaa aggtttgtcc aagaaagaac ttggaaaacg ctaagtttgg tttgtgggtt   660
gatggtaact gtgaagatat ccacatgtt aacgaatttt ccgctattga tttgtttgaa   720
tgtaacaagt tggttttttga attgtctgct tctgatcaac caagcaata cgaacaacat   780
ttgactgatt acgaaaagat taaggaaggt tttaagaaca agaacgctga tatgattaag   840
tctgcttttt tgccaactgg tgcttttaag gctgatagat acaagtctca tggtaagggt   900
tacaactggg gtaactacaa cagaaagact caaaagtgtg aaatttttaa cgttaagcca   960
acttgtttga ttaacgataa gtcttacatt gctactactg ctttgtctca tccaattgaa  1020
gttgaacata acttttccatg ttctttgtac aaggatgaaa ttaagaagga aattgaaaga  1080
gaatctaaga gaattaagtt gaacgataac gatgatgaag gtaacaagaa gattattgct  1140
ccaagaattt ttatttctga tgataaggat tctttgaagt gtccatgtga tccagaaatt  1200
gtttctcaat ctacttgtaa cttttttgtt tgtaagtgtg ttgaaaagag agctgaagtt  1260
acttctaaca acgaagttgt tgttaaggaa gaatacaagg atgaatacgc tgatattcca  1320
gaacataagc caacttacga taagatgtaa                                   1350
```

<210> SEQ ID NO 20
<211> LENGTH: 1350
<212> TYPE: DNA
<213> ORGANISM: Artificial
<220> FEATURE:
<223> OTHER INFORMATION: nucleic acid sequence encoding SEQ ID NO: 8

<400> SEQUENCE: 20

```
attgaaattg ttgaaagatc taactacatg ggtaacccat ggactgaata catggctaag    60
tacgatattg aagaagttca tggttctggt attagagttg atttgggtga agatgctgaa   120
gttgctggta ctcaatacag attgccatct ggtaagtgtc cagttttttgg taagggtatt  180
attattgaaa actctaagac tacttttttg actccagttg ctactgaaaa ccaagatttg   240
aaggatggtg gttttgcttt tccaccaact gaaccattga tttctccaat gactttgaac   300
ggtatgagag attttacaa gaacaacgaa tacgttaaga acttggatga attgactttg    360
tgttctagac atgctggtaa catgaaccca gataacgatg aaaactctaa ctacaagtac   420
ccagctgttt acgattacaa cgataagaag tgtcatattt tgtacattgc tgctcaagaa   480
aacaacggtc aagatactg taacaaggat gaatctaaga gaaactctat gttttgtttt    540
agaccagcta aggataagtt gtttgaaaac tacgtttact tgtctaagaa cgttgttgat   600
aactgggaaa aggtttgtcc aagaaagaac ttggaaaacg ctaagtttgg tttgtgggtt   660
```

```
gatggtaact gtgaagatat tccacatgtt aacgaattt ccgctaacga tttgtttgaa      720
tgtaacaagt tggttttga attgtctgct tctgatcaac caaagcaata cgaacaacat      780
ttgactgatt acgaaaagat taaggaaggt tttaagaaca agaacgctga tatgattaag     840
tctgcttttt tgccaactgg tgcttttaag gctgatagat acaagtctca tggtaagggt    900
tacaactggg gtaactacaa cagaaagact caaaagtgtg aaatttttaa cgttaagcca    960
acttgtttga ttaacgataa gtcttacatt gctactactg ctttgtctca tccaattgaa    1020
gttgaacata acttccatg ttctttgtac aagaacgaaa ttatgaagga aattgaaaga    1080
gaatctaaga gaattaagtt gaacgataac gatgatgaag gtaacaagaa gattattgct   1140
ccaagaattt ttatttctga tgataaggat tctttgaagt gtccatgtga tccagaaatt   1200 gttctctcaat ctacttgtaa cttttttgtt tgtaagtgtg ttgaaaagag agctgaagtt   1260
acttctaaca acgaagttgt tgttaaggaa gaatacaagg atgaatacgc tgatattcca   1320
gaacataagc caacttacga taagatgtaa                                     1350

<210> SEQ ID NO 21
<211> LENGTH: 1350
<212> TYPE: DNA
<213> ORGANISM: Artificial
<220> FEATURE:
<223> OTHER INFORMATION: nucleic acid sequence encoding SEQ ID NO: 9

<400> SEQUENCE: 21
attgaaattg ttgaaagatc taactacatg ggtaacccat ggactgaata catggctaag     60
tacgatattg aagaagttca tggttctggt attagagttg attgggtgaa agatgctgaa   120
gttgctggta ctcaatacag attgccatct ggtaagtgtc cagttttgg taagggtatt    180 attattgaaa actctcaaac tacttttttg aagccagttg ctactggtaa ccaagattg    240 aaggatggtg gttttgcttt tccaccaact aacccattga tgtctccaat gactttggat   300
gatatgagag atttgtacaa ggataacgaa tacgttaaga acttggatga attgactttg   360
tgttctagac atgctggtaa catgaaccca gataacgata gaactctaa ctacaagtac    420 ccagctgttt acgatgataa ggataagaag tgtcatattt tgtacattgc tgctcaagaa    480
aacaacggtc caagatactg taacaaggat caatctaaga gaaactctat gttttgtttt   540
agaccagcta aggatatttc ctttcaaaac tacgtttact tgtctaagaa cgttgttcat    600
aactgggaag aagtttgtcc aagaaagaac ttgcaaaacg ctaagtttgg tttgtggtt   660 gatggtaact gtgaagatat tccacatgtt aacgaattt ccgctaacga tttgtttgaa   720
tgtaacaagt tggttttga attgtctgct tctgatcaac caaagcaata cgaacaacat    780
ttgactgatt acgaaaagat taaggaaggt tttaagaaca agaacgctga tatgattaag    840
tctgcttttt tgccaactgg tgcttttaag gctgatagat acaagtctag aggtaagggt   900
tacaactggg gtaactacaa cactgaaact caaaagtgtg aaatttttaa cgttaagcca    960
acttgtttga ttaacgataa gtcttacatt gctactactg ctttgtctca tccaaacgaa   1020
gttgaaaaca acttccatg ttctttgtac aaggatgaaa ttaagaagga aattgaaaga   1080
gaatctaaga gaattaagtt gaacgataac gatgatgaag gtaacaagaa gattattgct   1140
ccaagaattt ttatttctga tgatattgat tctttgaagt gtccatgtgc tccagaaatg   1200
gtttctcaat ctacttgtag attttttgtt tgtaagtgtg ttgaaagaag agctgaagtt   1260
acttctaaca acgaagttgt tgttaaggaa gaatacaagg atgaatacgc tgatattcca   1320
gaacataagc caacttacga taacatgtaa                                     1350
```

<210> SEQ ID NO 22
<211> LENGTH: 1350
<212> TYPE: DNA
<213> ORGANISM: Artificial
<220> FEATURE:
<223> OTHER INFORMATION: nucleic acid sequence encoding SEQ ID NO: 10

<400> SEQUENCE: 22

```
attgaaattg ttgaaagatc taactacatg ggtaacccat ggactgaata catggctaag      60
tacgatattg aagaagttca tggttctggt attagagttg atttgggtga agatgctgaa     120
gttgctggta ctcaatacag attgccatct ggtaagtgtc cagtttttgg taagggtatt     180
attattgaaa actctaacac tacttttttg actccagttg ctactgaaaa ccaagatttg     240
aaggatggtg ttttgctttt ccaccaact aagccattga tgtctccaat gactttggat     300
caaatgagac attttacaa ggataacaag tacgttaaga acttggatga attgactttg     360
tgttctagac atgctggtaa catgattcca gataacgata agaactctaa ctacaagtac     420
ccagctgttt acgattacga agataagaag tgtcatattt tgtacattgc tgctcaagaa     480
aacaacggtc aagatactg taacaaggat gaatctaaga gaaactctat gttttgtttt     540
agaccagcta aggataagtc ctttcaaaac tacacttact tgtctaagaa cgttgttgat     600
aactgggaaa aggtttgtcc aagaaagaac ttggaaaacg ctaagtttgg tttgtgggtt     660
gatggtaact gtgaagatat ccacatgtt aacgaatttt ccgctattga tttgtttgaa     720
tgtaacaagt tggttttga attgtctgct tctgatcaac aaagcaata cgaacaacat     780
ttgactgatt acgaaaagat taaggaaggt tttaagaaca gaacgcttc catgattaag     840
tctgcttttt tgccaactgg tgcttttaag gctgatagat acaagtctca tggtaagggt     900
tacaactggg gtaactacaa cagaaagact caaaagtgtg aaattttaa cgttaagcca     960
acttgtttga ttaacaactc ctcttacatt gctactactg ctttgtctca tccaattgaa    1020
gttgaacata actttccatg ttctttgtac aaggatgaaa ttaagaagga aattgaaaga    1080
gaatctaaga gaattaagtt gaacgataac gatgatgaag gtaacaagaa gattattgct    1140
ccaagaattt ttatttctga tgataaggat tctttgaagt gtccatgtga tccagaaatt    1200
gtttctaact ctacttgtaa cttttttgtt tgtaagtgtg ttgaaaagag agctgaagtt    1260
acttctaaca acgaagttgt tgttaaggaa gaatacaagg atgaatacgc tgatattcca    1320
gaacataagc caacttacga taagatgtaa                                     1350
```

<210> SEQ ID NO 23
<211> LENGTH: 1350
<212> TYPE: DNA
<213> ORGANISM: Artificial
<220> FEATURE:
<223> OTHER INFORMATION: nucleic acid sequence encoding SEQ ID NO: 11

<400> SEQUENCE: 23

```
attgaaattg ttgaaagatc taactacatg ggtaacccat ggactgaata catggctaag      60
tacgatattg aagaagttca tggttctggt attagagttg atttgggtga agatgctgaa     120
gttgctggta ctcaatacag attgccatct ggtaagtgtc cagtttttgg taagggtatt     180
attattgaaa actctaagac tacttttttg actccagttg ctactgaaaa ccaagatttg     240
aaggatggtg ttttgctttt ccaccaact gaaccattga tttctccaat gactttgaac     300
ggtatgagag attttacaa gaacaacgaa tacgttaaga acttggatga attgactttg     360
tgttctagac atgctggtaa catgaaccca gataacgatg aaaactctaa ctacaagtac     420
```

```
ccagctgttt acgattacaa cgataagaag tgtcatattt tgtacattgc tgctcaagaa      480
aacaacggtc caagatactg taacaaggat gaatctaaga gaaactctat gttttgtttt      540
agaccagcta aggataagtt gtttgaaaac tacacttact tgtctaagaa cgttgttgat      600
aactgggaaa aggtttgtcc aagaaagaac ttggaaaacg ctaagtttgg tttgtgggtt      660
gatggtaact gtgaagatat tccacatgtt aacgaatttt ccgctaacga tttgtttgaa      720
tgtaacaagt tggttttga attgtctgct tctgatcaac aaagcaata cgaacaacat       780 ttgactgatt acgaaaagat taaggaaggt tttaagaaca gaacgcttc catgattaag      840 tctgcttttt tgccaactgg tgcttttaag gctgatagat acaagtctca tggtaagggt      900
tacaactggg gtaactacaa cagaaagact caaaagtgtg aaatttttaa cgttaagcca      960
acttgtttga ttaacaactc ctcttacatt gctactactg ctttgtctca tccaattgaa     1020
gttgaacata acttttccatg ttctttgtac aagaacgaaa ttatgaagga aattgaaaga   1080
gaatctaaga gaattaagtt gaacgataac gatgatgaag gtaacaagaa gattattgct     1140
ccaagaattt ttatttctga tgataaggat tctttgaagt gtccatgtga tccagaaatt     1200
gtttctaact ctacttgtaa cttttttgtt tgtaagtgtg ttgaaaagag agctgaagtt    1260
acttctaaca acgaagttgt tgttaaggaa gaatacaagg atgaatacgc tgatattcca     1320
gaacataagc caacttacga taagatgtaa                                      1350

<210> SEQ ID NO 24
<211> LENGTH: 1350
<212> TYPE: DNA
<213> ORGANISM: Artificial
<220> FEATURE:
<223> OTHER INFORMATION: nucleic acid sequence encoding SEQ ID NO: 12

<400> SEQUENCE: 24
attgaaattg ttgaaagatc taactacatg ggtaacccat ggactgaata catggctaag      60
tacgatattg aagaagttca tggttctggt attagagttg atttgggtga agatgctgaa     120
gttgctggta ctcaatacag attgccatct ggtaagtgtc cagtttttgg taagggtatt     180
attattgaaa actctaacac tactttttg aagccagttg ctactggtaa ccaagatttg     240
aaggatggtg gttttgcttt tccaccaact aacccattga tgtctccaat gactttggat    300
gatatgagag atttgtacaa ggataacgaa tacgttaaga acttggatga attgactttg     360
tgttctagac atgctggtaa catgaaccca gataacgata gaactctaa ctacaagtac     420 ccagctgttt acgatgataa ggataagaag tgtcatattt tgtacattgc tgctcaagaa    480
aacaacggtc caagatactg taacaaggat caatctaaga gaaactctat gttttgtttt    540
agaccagcta aggatatttc ctttcaaaac tacacttact tgtctaagaa cgttgttcat    600
aactgggaag aagtttgtcc aagaaagaac ttgcaaaacg ctaagtttgg tttgtgggtt    660
gatggtaact gtgaagatat tccacatgtt aacgaatttt ccgctaacga tttgtttgaa    720
tgtaacaagt tggttttga attgtctgct tctgatcaac aaagcaata cgaacaacat     780 ttgactgatt acgaaaagat taaggaaggt tttaagaaca gaacgcttc catgattaag    840 tctgcttttt tgccaactgg tgcttttaag gctgatagat acaagtctag aggtaagggt    900
tacaactggg gtaactacaa cactgaaact caaaagtgtg aaatttttaa cgttaagcca    960
acttgtttga ttaacaactc ctcttacatt gctactactg ctttgtctca tccaaacgaa   1020
gttgaaaaca cttttccatg ttctttgtac aaggatgaaa ttaagaagga aattgaaaga   1080
gaatctaaga gaattaagtt gaacgataac gatgatgaag gtaacaagaa gattattgct   1140
```

```
ccaagaattt ttatttctga tgatattgat tctttgaagt gtccatgtgc tccagaaatg    1200
gtttctaact ctacttgtag attttttgtt tgtaagtgtg ttgaaagaag agctgaagtt    1260
acttctaaca acgaagttgt tgttaaggaa gaatacaagg atgaatacgc tgatattcca    1320
gaacataagc caacttacga taacatgtaa                                    1350
```

<210> SEQ ID NO 25
<211> LENGTH: 449
<212> TYPE: PRT
<213> ORGANISM: Artificial
<220> FEATURE:
<223> OTHER INFORMATION: consensus sequence AMA1 plasmodium falciparum

<400> SEQUENCE: 25

```
Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Asn Thr Thr Phe Leu Thr Pro Val Ala Thr Glu Asn Gln Asp Leu
65                  70                  75                  80

Lys Asp Gly Gly Phe Ala Phe Pro Pro Thr Asn Pro Leu Met Ser Pro
                85                  90                  95

Met Thr Leu Asp Gln Met Arg Asp Phe Tyr Lys Asp Asn Glu Tyr Val
            100                 105                 110

Lys Asn Leu Asp Glu Leu Thr Leu Cys Ser Arg His Ala Gly Asn Met
        115                 120                 125

Asn Pro Asp Asn Asp Lys Asn Ser Asn Tyr Lys Tyr Pro Ala Val Tyr
    130                 135                 140

Asp Tyr Lys Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Ser Phe Gln Asn Tyr Thr
            180                 185                 190

Tyr Leu Ser Lys Asn Val Val Asp Asn Trp Glu Lys Val Cys Pro Arg
        195                 200                 205

Lys Asn Leu Glu Asn Ala Lys Phe Gly Leu Trp Val Asp Gly Asn Cys
    210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Ser Met Ile Lys Ser Ala Phe Leu Pro Thr Gly Ala
        275                 280                 285

Phe Lys Ala Asp Arg Tyr Lys Ser His Gly Lys Gly Tyr Asn Trp Gly
    290                 295                 300

Asn Tyr Asn Arg Lys Thr Gln Lys Cys Glu Ile Phe Asn Val Lys Pro
305                 310                 315                 320

Thr Cys Leu Ile Asn Asn Ser Ser Tyr Ile Ala Thr Thr Ala Leu Ser
                325                 330                 335
```

His Pro Ile Glu Val Glu His Asn Phe Pro Cys Ser Leu Tyr Lys Asp
                340                 345                 350

Glu Ile Lys Lys Glu Ile Glu Arg Glu Ser Lys Arg Ile Lys Leu Asn
            355                 360                 365

Asp Asn Asp Asp Glu Gly Asn Lys Lys Ile Ile Ala Pro Arg Ile Phe
370                 375                 380

Ile Ser Asp Asp Lys Asp Ser Leu Lys Cys Pro Cys Asp Pro Glu Ile
385                 390                 395                 400

Val Ser Asn Ser Thr Cys Asn Phe Phe Val Cys Lys Cys Val Glu Lys
                405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Lys
                435                 440                 445

Met

<210> SEQ ID NO 26
<211> LENGTH: 28
<212> TYPE: DNA
<213> ORGANISM: Artificial
<220> FEATURE:
<223> OTHER INFORMATION: X1 primer sequence

<400> SEQUENCE: 26
gcgaattcat tgaaattgtt gaaagatc                                    28

<210> SEQ ID NO 27
<211> LENGTH: 28
<212> TYPE: DNA
<213> ORGANISM: Artificial
<220> FEATURE:
<223> OTHER INFORMATION: Y1 primer sequence

<400> SEQUENCE: 27
ggggtaccaa catcttatcg taagttgg                                    28

<210> SEQ ID NO 28
<211> LENGTH: 29
<212> TYPE: DNA
<213> ORGANISM: Artificial
<220> FEATURE:
<223> OTHER INFORMATION: Y2 primer sequence

<400> SEQUENCE: 28
ggggtaccga catgttatcg taagttggc                                   29

<210> SEQ ID NO 29
<211> LENGTH: 449
<212> TYPE: PRT
<213> ORGANISM: Plasmodium falciparum

<400> SEQUENCE: 29

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
                20                  25                  30

Val Asp Leu Gly Glu Asp Ala Glu Val Ala Gly Thr Gln Tyr Arg Leu
            35                  40                  45

Pro Ser Gly Lys Cys Pro Val Phe Gly Lys Gly Ile Ile Ile Glu Asn
        50                  55                  60

Ser Lys Thr Thr Phe Leu Thr Pro Val Ala Thr Gly Asn Gln Tyr Leu
65                  70                  75                  80

Lys Asp Gly Gly Phe Ala Phe Pro Pro Thr Glu Pro Leu Met Ser Pro
            85                  90                  95

Met Thr Leu Asp Glu Met Arg His Phe Tyr Lys Asp Asn Lys Tyr Val
            100                 105                 110

Lys Asn Leu Asp Glu Leu Thr Leu Cys Ser Arg His Ala Gly Asn Met
        115                 120                 125

Ile Pro Asp Asn Asp Lys Asn Ser Asn Tyr Lys Tyr Pro Ala Val Tyr
        130                 135                 140

Asp Asp Lys Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Ile Ser Phe Gln Asn Tyr Val
            180                 185                 190

Tyr Leu Ser Lys Asn Val Val Asp Asn Trp Glu Lys Val Cys Pro Arg
        195                 200                 205

Lys Asn Leu Gln Asn Ala Lys Phe Gly Leu Trp Val Asp Gly Asn Cys
    210                 215                 220

Glu Asp Ile Pro His Val Asn Glu Phe Pro Ala Ile Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Asp Met Ile Lys Ser Ala Phe Leu Pro Thr Gly Ala
        275                 280                 285

Phe Lys Ala Asp Arg Tyr Lys Ser His Gly Lys Gly Tyr Asn Trp Gly
    290                 295                 300

Asn Tyr Asn Thr Glu Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                325                 330                 335

His Pro Ile Glu Val Glu Asn Asn Phe Pro Cys Ser Leu Tyr Lys Asp
            340                 345                 350

Glu Ile Met Lys Glu Ile Glu Arg Glu Ser Lys Arg Ile Lys Leu Asn
        355                 360                 365

Asp Asn Asp Asp Glu Gly Asn Lys Lys Ile Ile Ala Pro Arg Ile Phe
    370                 375                 380

Ile Ser Asp Asp Lys Asp Ser Leu Lys Cys Pro Cys Asp Pro Glu Met
385                 390                 395                 400

Val Ser Gln Ser Thr Cys Arg Phe Phe Val Cys Lys Cys Val Glu Arg
                405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Lys
        435                 440                 445

Met

<210> SEQ ID NO 30
<211> LENGTH: 449
<212> TYPE: PRT
<213> ORGANISM: Plasmodium falciparum

<400> SEQUENCE: 30

```
Ile Glu Ile Val Glu Arg Ser Asn Tyr Met Gly Asn Pro Trp Thr Glu
1               5                   10                  15
Tyr Met Ala Lys Tyr Asp Ile Glu Lys Val His Gly Ser Gly Ile Arg
            20                  25                  30
Val Asp Leu Gly Glu Asp Ala Glu Val Ala Gly Thr Gln Tyr Arg Leu
        35                  40                  45
Pro Ser Gly Lys Cys Pro Val Phe Gly Lys Gly Ile Ile Ile Glu Asn
    50                  55                  60
Ser Lys Thr Thr Phe Leu Thr Pro Val Ala Thr Glu Asn Gln Asp Leu
65                  70                  75                  80
Lys Asp Gly Gly Phe Ala Phe Pro Pro Thr Glu Pro Leu Ile Ser Pro
                85                  90                  95
Met Thr Leu Asp Gln Met Arg His Leu Tyr Lys Asp Asn Glu Tyr Val
            100                 105                 110
Lys Asn Leu Asp Glu Leu Thr Leu Cys Ser Arg His Ala Gly Asn Met
        115                 120                 125
Asn Pro Asp Asn Asp Lys Asn Ser Asn Tyr Lys Tyr Pro Ala Val Tyr
    130                 135                 140
Asp Tyr Glu Asp Lys Lys Cys His Ile Leu Tyr Ile Ala Ala Gln Glu
145                 150                 155                 160
Asn Asn Gly Pro Arg Tyr Cys Asn Lys Asp Glu Ser Lys Arg Asn Ser
                165                 170                 175
Met Phe Cys Phe Arg Pro Ala Lys Asp Lys Leu Phe Glu Asn Tyr Val
            180                 185                 190
Tyr Leu Ser Lys Asn Val Val Asp Asn Trp Glu Glu Val Cys Pro Arg
        195                 200                 205
Lys Asn Leu Glu Asn Ala Lys Phe Gly Leu Trp Val Asp Gly Asn Cys
    210                 215                 220
Glu Asp Ile Pro His Val Asn Glu Phe Ser Ala Asn Asp Leu Phe Glu
225                 230                 235                 240
Cys Asn Lys Leu Val Phe Glu Leu Ser Ala Ser Asp Gln Pro Lys Gln
                245                 250                 255
Tyr Glu Gln His Leu Thr Asp Tyr Glu Lys Ile Lys Glu Gly Phe Lys
            260                 265                 270
Asn Lys Asn Ala Asp Met Ile Lys Ser Ala Phe Leu Pro Thr Gly Ala
        275                 280                 285
Phe Lys Ala Asp Arg Tyr Lys Ser Arg Gly Lys Gly Tyr Asn Trp Gly
    290                 295                 300
Asn Tyr Asn Thr Glu Thr Gln Lys Cys Glu Ile Phe Asn Val Lys Pro
305                 310                 315                 320
Thr Cys Leu Ile Asn Asp Lys Ser Tyr Ile Ala Thr Thr Ala Leu Ser
                325                 330                 335
His Pro Asn Glu Val Glu Asn Asn Phe Pro Cys Ser Leu Tyr Lys Asp
            340                 345                 350
Glu Ile Lys Lys Glu Ile Glu Arg Glu Ser Lys Arg Ile Lys Leu Asn
        355                 360                 365
Asp Asn Asp Asp Glu Gly Asn Lys Lys Ile Ile Ala Pro Arg Ile Phe
    370                 375                 380
Ile Ser Asp Asp Lys Asp Ser Leu Lys Cys Pro Cys Asp Pro Glu Ile
385                 390                 395                 400
Val Ser Gln Ser Thr Cys Asn Phe Phe Val Cys Lys Cys Val Glu Lys
                405                 410                 415
```

```
Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Lys
            435                 440                 445

Met

<210> SEQ ID NO 31
<211> LENGTH: 449
<212> TYPE: PRT
<213> ORGANISM: Plasmodium falciparum

<400> SEQUENCE: 31

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Glu Asn
    50                  55                  60

Ser Lys Thr Thr Phe Leu Lys Pro Val Ala Thr Gly Asn Gln Asp Leu
65                  70                  75                  80

Lys Asp Gly Gly Phe Ala Phe Pro Pro Thr Asn Pro Leu Ile Ser Pro
                85                  90                  95

Met Thr Leu Asn Gly Met Arg Asp Phe Tyr Lys Asn Asn Glu Tyr Val
            100                 105                 110

Lys Asn Leu Asp Glu Leu Thr Leu Cys Ser Arg His Ala Gly Asn Met
        115                 120                 125

Asn Pro Asp Asn Asp Lys Asn Ser Asn Tyr Lys Tyr Pro Ala Val Tyr
    130                 135                 140

Asp Tyr Asn Asp Lys Lys Cys His Ile Leu Tyr Ile Ala Ala Gln Glu
145                 150                 155                 160

Asn Asn Gly Pro Arg Tyr Cys Asn Lys Asp Gln Ser Lys Arg Asn Ser
                165                 170                 175

Met Phe Cys Phe Arg Pro Ala Lys Asp Lys Leu Phe Glu Asn Tyr Val
            180                 185                 190

Tyr Leu Ser Lys Asn Val Val Asp Asn Trp Glu Glu Val Cys Pro Arg
        195                 200                 205

Lys Asn Leu Glu Asn Ala Lys Phe Gly Leu Trp Val Asp Gly Asn Cys
    210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Asp Met Ile Lys Ser Ala Phe Leu Pro Thr Gly Ala
        275                 280                 285

Phe Lys Ala Asp Arg Tyr Lys Ser His Gly Lys Gly Tyr Asn Trp Gly
    290                 295                 300

Asn Tyr Asn Arg Glu Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                325                 330                 335

His Pro Ile Glu Val Glu His Asn Phe Pro Cys Ser Leu Tyr Lys Asp
```

-continued

```
                340                 345                 350
Glu Ile Lys Lys Glu Ile Glu Arg Glu Ser Lys Arg Ile Lys Leu Asn
        355                 360                 365

Asp Asn Asp Asp Glu Gly Asn Lys Lys Ile Ile Ala Pro Arg Ile Phe
        370                 375                 380

Ile Ser Asp Asp Lys Asp Ser Leu Lys Cys Pro Cys Asp Pro Glu Met
385                 390                 395                 400

Val Ser Gln Ser Thr Cys Arg Phe Phe Val Cys Lys Cys Val Glu Arg
                405                 410                 415

Arg Ala Glu Val Thr Ser Asn Asn Glu Val Val Val Lys Glu Glu Tyr
                420                 425                 430

Lys Asp Glu Tyr Ala Asp Ile Pro Glu His Lys Pro Thr Tyr Asp Lys
        435                 440                 445

Met
```